(12) United States Patent
Rinaudo et al.

(10) Patent No.: US 8,039,447 B2
(45) Date of Patent: Oct. 18, 2011

(54) DERIVATIVES OF HYALURONIC ACID, THEIR PREPARATION PROCESS AND THEIR USES

(75) Inventors: Marguerite Rinaudo, Grenoble (FR); Rachel Auzely, St Georges de Commiers (FR); Shirin Kadi, Grenoble (FR); Anthony Bresin, Reims (FR); Erell Kubik, Sorbon (FR)

(73) Assignees: Centre National de la Recherche Scientifique (C.N.R.S.), Paris (FR); Agro Industrie Recherches et Developpements A.R.D., Pomacle (FR)

( * ) Notice: Subject to any disclaimer, the term of this patent is extended or adjusted under 35 U.S.C. 154(b) by 617 days.

(21) Appl. No.: 12/094,159

(22) PCT Filed: Nov. 16, 2006

(86) PCT No.: PCT/EP2006/010991
§ 371 (c)(1),
(2), (4) Date: Aug. 13, 2008

(87) PCT Pub. No.: WO2007/059890
PCT Pub. Date: May 31, 2007

(65) Prior Publication Data
US 2008/0306023 A1 Dec. 11, 2008

(30) Foreign Application Priority Data
Nov. 22, 2005 (EP) .................................... 05292474

(51) Int. Cl.
*A61K 31/726* (2006.01)
*A61K 31/738* (2006.01)
*A61F 2/14* (2006.01)

(52) U.S. Cl. ............................ 514/54; 536/55.2; 623/4.1

(58) Field of Classification Search ........................ None
See application file for complete search history.

(56) References Cited

U.S. PATENT DOCUMENTS
7,767,806 B2 * 8/2010 Hirakura et al. ........... 536/123.1
2004/0234497 A1 * 11/2004 Luo et al. .................... 424/85.1

FOREIGN PATENT DOCUMENTS
WO 0016818 3/2000
WO 0206373 1/2002
WO WO 2005/023906 * 3/2005

OTHER PUBLICATIONS

Tian W M et al., "Hyaluronic acid hydrogel as Nogo-66 receptor antibody delivery system for the repairing of injured rat brain: in vitro", Journal of Controlled Release, Elsevier, Amsterdam, NL, vol. 102, No. 1, Jan. 20, 2005, Abstract.
International search report in corresponding PCT/EP2006/010991, (2007).

* cited by examiner

*Primary Examiner* — Leigh Maier
(74) *Attorney, Agent, or Firm* — Young & Thompson

(57) ABSTRACT

The present invention relates to the use of a compound having the formula (I) wherein: n represents an integer varying from 720 to 6 200, and i varies from 1 to n, $R_i$ represents in particular OH, or a group of the formula (III) wherein k represents an integer varying from 1 to 17, and $R'_i$ represents a linear or branched alkyl chain comprising p carbon atoms, wherein p is an integer varying from 1 to 17, with the proviso that k+p is not greater than 28, and preferably not greater than 20, and wherein at least one $R_i$ group represents a group of formula (III), for the preparation of a viscoelastic composition.

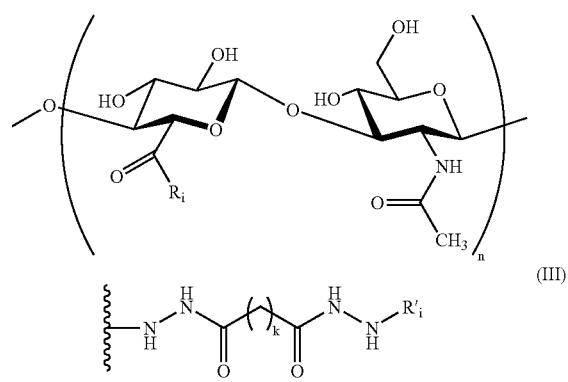

18 Claims, 11 Drawing Sheets

DERIVATIVES OF HYALURONIC ACID, THEIR PREPARATION PROCESS AND THEIR USES

The present invention relates to new derivatives of hyaluronic acid, and to their preparation process thereof. It also relates to uses of said new derivatives, in particular in the pharmaceutical field.

Hydrophobically modified water soluble polymers that associate in solution via physical interactions are often efficient rheology modifiers (*Polymers in Aqueous Media: Performance through Association*; Glass, J. E., Ed.; Advances in Chemistry Series 223; American Chemical Society: Washington, D.C., 1989; *Polymers as Rheology Modifiers*; Schulz, D. N., Glass, J. E., Eds.; ACS Symposium Series 462; American Chemical Society Washington, D.C., 1991; Winnik, M. A.; Yekta, A. *Curr. Opin. Colloid Interface Sci.* 1997, 2, 424). These are used as thickening agents in many fields of applications such as paints, cosmetics, foods, oil recovery. The main microstructural feature of such polymers is their ability to give rise to weak intra and intermolecular hydrophobic interactions in aqueous solutions. In the semi-dilute regime, these intermolecular associations are predominant. Very viscous solutions or physical gels exhibiting a shear thinning behaviour can thus be obtained. With hydrophobically modified polyelectrolytes, the viscosity of the solution can also be enhanced by several orders of magnitude upon addition of salt unlike to non-associating polyelectrolytes with which a decrease of the viscosity is usually observed. Numerous studies have been devoted to synthetic associating polyelectrolytes. However, in spite of the numerous applications which may be offered by naturally occurring polyelectrolytes with associative groups in the fields of food industry, pharmacy, cosmetology, and medicine, few types of such polymers have been proposed (Sinquin, A.; Hubert, P.; Marchal, P.; Choplin, L.; Dellacherie, E. *Colloid Surf A* 1996, 112, 193; Fischer, A.; Houzelle, M. C.; Hubert, P.; Axelos, M. A. V.; Geoffroy-Chapotot, C.; Carre, M. C.; Viriot, M. L.; Dellacherie, E. *Langmuir* 1998, 14, 4482; Pelletier, S.; Hubert, P.; Payan, E.; Marchal, P.; Choplin, L.; Dellacherie, E. *J. Biomed. Mat. Res.* 2001, 54, 102; Desbrières, J.; Martinez, C.; Rinaudo, M. *Int. J. Biol. Macromol.* 1996, 19, 21; Desbrières, J.; Rinaudo, M.; Babak, V.; Vikhoreva, G. *Polym. Bull.* 1997, 39, 209; Auzély, R.; Rinaudo, M. *Macromol. Biosci.* 2003, 3, 562).

Hyaluronic acid (HA) is a linear polysaccharide composed of repeating disaccharide units of N-acetyl-D-glucosamine and D-glucuronic acid, belonging to the glycosaminoglycan family, said repeating unit having the following formula:

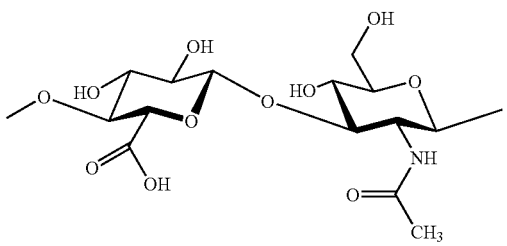

It is a component of the synovial fluid, cartilage, vitreous humor and extracellular matrices, where it plays important structural and biological roles. Hyaluronic acid production was traditionally based on an extraction process from human or animal tissues. Umbilical cords, rooster combs or bovine vitreous humor were widely used as raw material to provide high molecular weight hyaluronic acid for various applications in the pharmaceutical and cosmetic industries. However, the extraction process from human or animal feedstocks does not allow the production of safe HA from risks of virus infection. Moreover, it is difficult to obtain pure HA in an economically viable way because of complexes formation with proteoglycans from animal tissues (O'Regan, M., Martini, I., Crescenzi, F., De Luca, C., and Lansing, M. (1994). Molecular mechanisms and genetics of hyaluronan biosynthesis. International Journal of Biological Macromolecules 16, 283-286.).

Nowadays, the production process is not only based on an extraction process from human or animal raw material but also on biotechnological processes using micro organisms as HA producers. Some strains such as Group C *Streptococcus equisimilis*, or *Pasteurella multocida* have the ability to produce HA from various carbohydrates. Various processes of fermentation have been described in the literature or patented (KR8701815, DE10019868, JP2000189186) but they are all based on the same pathway:

- the use of a GMO (genetically modified organism) or non-GMO strain of bacterial or yeast,
- a carbon source coming from carbohydrates (e.g.: glucose, fructose . . . ) for the growth of the strain and the HA production,
- a nitrogen source (animal or vegetable) for the growth of the strain and the HA production,
- the use of reactor (fermentor) with controlled conditions,
- a purification process to remove cells from the fermentation broth,
- a purification process to recover the HA from the fermentation broth.

Viscosupplementation is the most widespread use of HA. It is used to replace the pathologic synovial fluid and supplement the elasticity and viscosity of the endogenous hyaluronic acid. (Balazs EA. The physical properties of synovial fluid and the special role of hyaluronic acid. In helfet AJ (ed) Disorders of the knee 2edn. Philadelphia: JB Lippincott, 1982; 61-74).

A key point for the success of knee pain treatment during osteoarthritis is the preservation of the rheological properties of the HA as long as possible in order to avoid repetitive injections and the risk of bioaccumulation of non biodegradable residues of chemically modified HA.

Among the different hyaluronic acid used in viscosupplementation of synovial fluid of arthritic joints, we may cite Synvisc® (Genzyme), Orthovisc® (Anika Therapeutics), Arthrum® (LCA, France), Hyalgan® (Sanofi Aventis), Supartz® (Smith&Nephew) and Adant® (Tedec Meiji Farma SA, Espagne).

Synvisc® G-F20 is composed of 80% Hylan A fluid and 20% Hylan B gel prepared via chemically cross-linked hyaluronic acid (from rooster combs). The Synvisc® is specifically designed to have a high percentage of elasticity over the entire frequency range of physiologic movements. Thus, this HA preparation has been approved for intra-articular injection in symptomatic patients with osteoarthritis of the knee (U.S. Pat. Nos. 5,099,013 and 4,713,448).

Orthovisc® is a viscous sterile solution made from highly purified hyaluronan from rooster combs, consisting of high molecular weight (1.0-2.9 million daltons), dissolved in physiological saline, which is also indicated in the treatment of pain in osteoarthritis of the knee.

Arthrum® is a sterile solution of bacterial hyaluronic acid of molecular weight of 2.4 millions Daltons.

Hyalgan® is an ultrapure high-molecular weight hyaluronan from rooster combs, with the molecular weight of 0.5 million Daltons on the average, and this HA preparation has been approved for intra-articular injection in symptomatic patients with osteoarthritis of the knee.

The natural HA are linear chains and have a relatively low viscosity, while Synvisc® contains a fraction of gel. Synvisc® becomes more stable against hydrolytic agents but includes non-biodegradable chemical junctions.

The aim of the invention is to provide new derivatives of hyaluronic acid that could be used in viscosupplementation, in particular in viscosupplementation of synovial fluid of arthritic joints.

The aim of the invention is to provide new derivatives of hyaluronic acid carrying alkyl groups.

The aim of the invention is also to provide a new process for the preparation of said derivatives of hyaluronic acid, said process having a good yield.

The present invention relates to the use of a compound having the following formula (I):

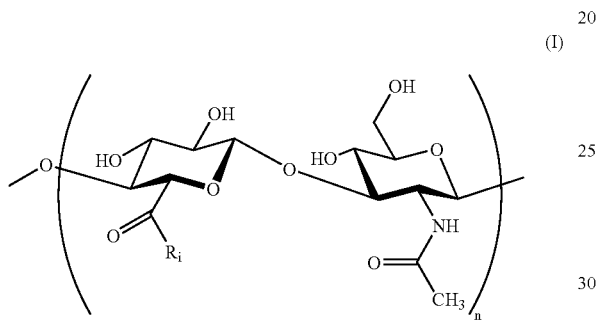

(I)

wherein:
n represents an integer varying from 720 to 6 200, preferably from 1 900 to 3 800, and in particular from 1 400 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation,
  or
  a group of the following formula (II):

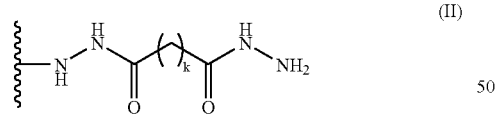

(II)

wherein:
k represents an integer varying from 1 to 17, and is in particular equal to or greater than 4,
or a group of the following formula (III'):

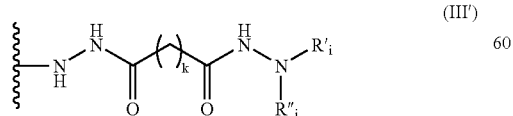

(III')

wherein:
k represents an integer varying from 1 to 17, and is in particular equal to or greater than 4,
$R'_i$ represents a linear or branched alkyl chain comprising p carbon atoms, or a ring comprising p carbon atoms, such as adamantane, wherein p is an integer varying from 1 to 17, and is in particular equal to or greater than 7, and preferably is 10,
$R''_i$ represents H or a linear or branched alkyl chain comprising p' carbon atoms, wherein p' is an integer varying from 1 to 17, and is in particular equal to or greater than 7, and preferably is 10, with the proviso that k+p+p' is not greater than 28, and preferably not greater than 20, and wherein at least one $R_i$ group represents a group of formula (III'), for the preparation of a viscoelastic composition.

The present invention relates to the use of a compound having the following formula (I):

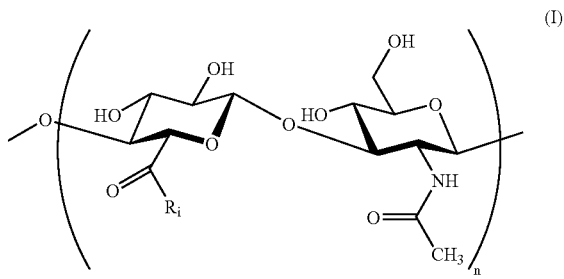

(I)

wherein:
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation,
  or
  a group of the following formula (II):

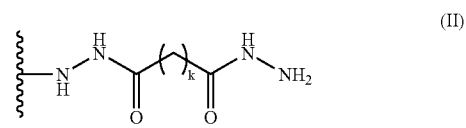

(II)

wherein:
k represents an integer varying from 1 to 17, and is in particular equal to or greater than 4,
or a group of the following formula (III):

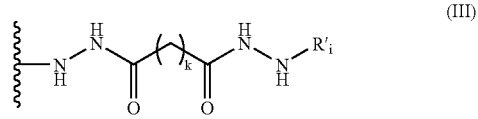

(III)

wherein:
k represents an integer varying from 1 to 17, and is in particular equal to or greater than 4,
$R'_i$ represents a linear or branched alkyl chain comprising p carbon atoms, wherein p is an integer varying from 1 to 17, and is in particular equal to or greater than 7, and preferably is 10, with the proviso that k+p is not greater than 28, and preferably not greater than 20, and wherein at least one $R_i$ group represents a group of formula (III), for the preparation of a viscoelastic composition.

When Z as mentioned above represents a divalent counterion, it may induce interchain crosslink and decrease the solubility.

The above-mentioned compounds of formula (I) have a molecular weight varying from about 300 000 to $2.5 \times 10^6$ g.mol$^{-1}$, preferably from 800 000 to $1.5 \times 10^6$ g.mol$^{-1}$.

According to the above-mentioned formula (I), the compounds of formula (I) are compounds containing a repetition of n motifs, wherein one motif has the following formula:

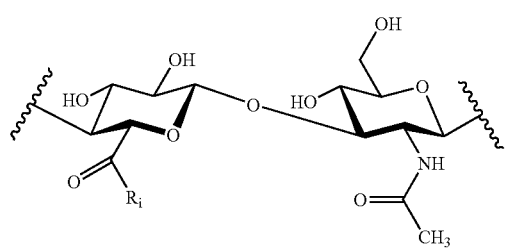

Thus, in formula (I), each motif "i" contains a group $R_i$. Each motif can contain a $R_i$ group varying for each motif as mentioned above, and thus the $R_i$ groups correspond to $R_1$ for the first motif, to $R_2$ for the second motif, to $R_3$ for the third motif, and to $R_n$ for the last motif (numbered n).

According to an advantageous embodiment, the invention relates to the use of compounds of formula (I) wherein n represents an integer varying from 720 to 6 250.

According to a more advantageous embodiment, the invention relates to the use of compounds of formula (I) wherein n represents an integer varying from 1 900 to 3 700, and preferably from 2 000 to 3 800.

According to an advantageous embodiment, in the above-mentioned formulae (II) and (III), k represents an integer varying from 2 to 12.

The compounds of formula (I) as defined above wherein k is greater than 17, or wherein p is greater than 17, or k+p is greater than 28 are non-soluble compounds in aqueous solutions.

According to an advantageous embodiment, in the above-mentioned formula (III), $R'_i$ represents a linear or branched alkyl chain comprising from 3 to 16 carbon atoms.

The present invention relates to the use of compounds of formula (I) as mentioned above wherein at least one $R_i$ group represents a group of formula (III). Thus, the present invention relates to the use of compounds as mentioned above wherein at least one motif numbered "i" contains a group of formula (III).

The value of k+p is defined for a given $R_i$ group (or for a given $R'_i$ group).

According to an advantageous embodiment, the present invention relates to the use of compounds of formula (I) as mentioned above, wherein k+p ranges from 11 to 28, and preferably from 11 to 20.

The modified HA of the invention (compounds of formula (I)) contain mobile junctions that increase the elasticity of the system and offer a self-repairing character.

The viscoelasticity is a characteristic of polymer solutions given by dynamic rheology; this characteristic is linked to the existence of an elastic component (G') and a viscous component (G") in the response of the material to the stress applied.

A gel is a 3D network; it can be crosslinked by chemical reaction or physical interaction. Chemical gels are stabilized by covalent bonds (G'>G" for any frequency) while physical gels are stabilized by reversible secondary bonds as hydrogen, van der Walls, hydrophobic, etc. . . . In these conditions, G' is greater than G" in a given domain of frequencies larger than $\omega_0$ (critical frequency) characteristic of each system in given experimental conditions.

The present invention relates to the use of a compound having the following formula (I):

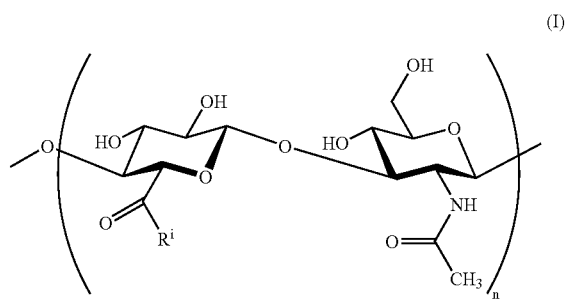

wherein:
n represents an integer varying from 720 to 6 200, preferably from 1 900 to 3 800,
i varies from 1 to n,
$R_i$ represents:
  OH,
  OZ, wherein Z represents any monovalent counterion such as Na$^+$ or K$^+$ or any divalent counterion such as Ca$^{2+}$ or Mg$^{2+}$, and is preferably a monovalent cation,
  or
  a group of the following formula (II):

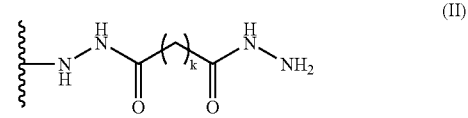

wherein:
  k represents an integer varying from 1 to 17, preferably from 2 to 12, and is in particular equal to or greater than 4,
or a group of the following formula (III'):

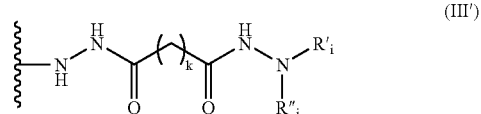

wherein:
  k represents an integer varying from 1 to 17, and is in particular equal to or greater than 4,
  $R'_i$ represents a linear or branched alkyl chain comprising p carbon atoms, or a ring comprising p carbon atoms, such as adamantane, wherein p is an integer varying from 1 to 17, and is in particular equal to or greater than 7, and preferably is 10,
  $R''_i$ represents H or a linear or branched alkyl chain comprising p' carbon atoms, wherein p' is an integer varying from 1 to 17, and is in particular equal to or greater than 7, and preferably is 10, with the proviso that k+p+p' is not greater than 28, and preferably not greater than 20,
and wherein at least one $R_i$ group represents a group of formula (III'), for the manufacture of a drug for cell culture, tissue engineering, soft tissue augmentation such as correction of facial wrinkles and scars, for viscosurgery, such as eye surgery, for viscoprotection, for viscoseparation in post surgical applications, for passive drug delivery, and for viscosupplementation, in particular for the treatment of arthrosis, such as knee arthrosis.

The viscoelastic properties of this material can be used to facilitate surgical procedures (viscosurgery), to protect delicate tissue surfaces (viscoprotection), to diminish adhesion formation (viscoseparation in post surgical applications), and to reduce pain and restore function in arthritic joints (viscosupplementation).

The performance of a fluid for viscosupplementation is characterized by rheology. The rheological profile (G': storage modulus and G": loss modulus as a function of the stress applied frequency) of a viscoelastic fluid is such as at low frequency G">G' and over a critical frequency ($\omega_0$ in Hz), G' becomes larger than G".

At low frequencies, a synovial fluid in a healthy joint behaves predominantly as a viscous fluid; during physiologic movement, and when subjected to stresses somewhat less than those occurring in slow walking ($\omega$=0.5 Hz), the material begins to act (at the crossover point) predominantly as an elastic solid (G'>G").

In pathological synovial fluids (e.g., arthritic joint), the fluid behaves predominantly as a viscous fluid and does not provide the tissue with the protection of an elastic solid when subjected to physiologic deformation forces.

The present invention relates to the use of a compound having the following formula (I):

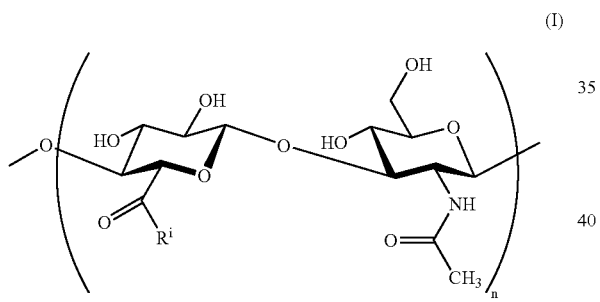

(I)

wherein:
n represents an integer varying from 720 to 6 200, preferably from 1 900 to 3 800,
i varies from 1 to n,
$R_i$ represents:
  OH,
  OZ, wherein Z represents any monovalent counterion such as Na$^+$ or K$^+$ or any divalent counterion such as Ca$^{2+}$ or Mg$^{2+}$, and is preferably a monovalent cation, or
  a group of the following formula (II):

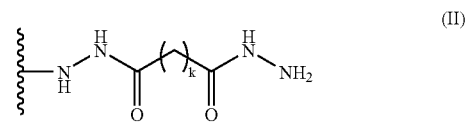

(II)

wherein:
k represents an integer varying from 1 to 17, preferably from 2 to 12, and is in particular equal to or greater than 4, or a group of the following formula (III):

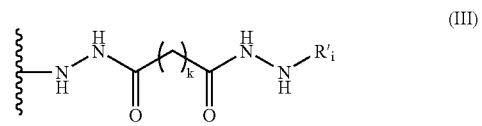

(III)

wherein:
k represents an integer varying from 1 to 17, and is in particular equal to or greater than 4,
$R'_i$ represents a linear or branched alkyl chain comprising p carbon atoms, wherein p is an integer varying from 1 to 17, and is in particular equal to or greater than 7, and preferably is 10,
with the proviso that k+p is not greater than 28, and preferably not greater than 20, and wherein at least one $R_i$ group represents a group of formula (III), for the manufacture of a drug for cell culture, tissue engineering, soft tissue augmentation such as correction of facial wrinkles and scars, for viscosurgery, such as eye surgery, for viscoprotection, for viscoseparation in post surgical applications, for passive drug delivery, and for viscosupplementation, in particular for the treatment of arthrosis, such as knee arthrosis.

The present invention also relates to the use of a compound having the following formula (I):

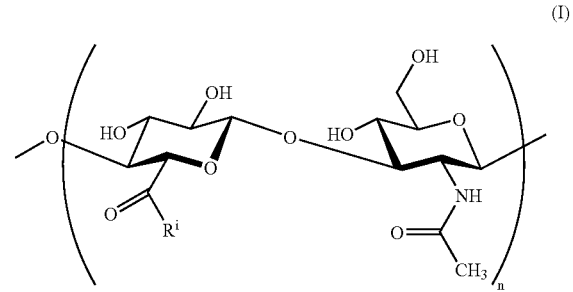

(I)

wherein:
n represents an integer varying from 720 to 6 200, preferably from 1 900 to 3 800,
i varies from 1 to n,
$R_i$ represents:
  OH,
  OZ, wherein Z represents any monovalent counterion such as Na$^+$ or K$^+$ or any divalent counterion such as Ca$^{2+}$ or Mg$^{2+}$, and is preferably a monovalent cation, or
  a group of the following formula (II):

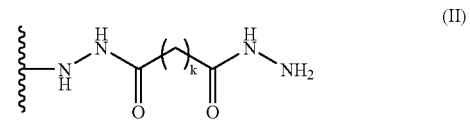

(II)

wherein:
k represents an integer varying from 1 to 17, or a group of the following formula (III):

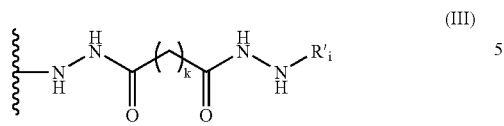

(III)

wherein:

k represents an integer varying from 1 to 17, $R'_i$ represents a linear or branched alkyl chain comprising p carbon atoms, wherein p is an integer varying from 1 to 6, with the proviso that k+p is not greater than 20, and wherein at least one $R_i$ group represents a group of formula (III), for the preparation of a viscoelastic composition.

According to an advantageous embodiment, the present invention relates to the use as mentioned above of a compound of formula (I), wherein k represents an integer varying from 1 to 12.

According to an advantageous embodiment, the present invention relates to the use as mentioned above of a compound of formula (I), wherein k represents an integer varying from 1 to 12, and wherein p is an integer varying from 1 to 6.

The present invention also relates to the use of a compound having the following formula (I):

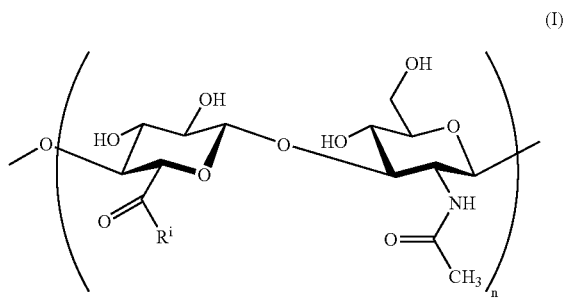

(I)

wherein:

n represents an integer varying from 720 to 6 200, preferably from 1 900 to 3 700, i varies from 1 to n, $R_i$ represents:

OH,

OZ, wherein Z represents any monovalent counterion such as $Na^+$ or $K^+$ or any divalent counterion such as $Ca^{2+}$ or $Mg^{2+}$, and is preferably a monovalent cation, or a group of the following formula (II):

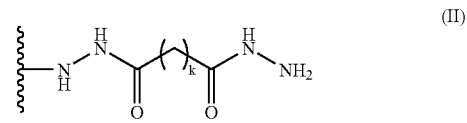

(II)

wherein k represents an integer varying from 1 to 17, or a group of the following formula (III):

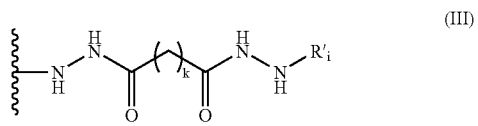

(III)

wherein:

k represents an integer varying from 1 to 17, $R'_i$ represents a linear or branched alkyl chain comprising p carbon atoms, wherein p is an integer varying from 1 to 6, with the proviso that k+p is not greater than 20, and wherein at least one $R_i$ group represents a group of formula (III), for the manufacture of a drug for cell culture, tissue engineering, soft tissue augmentation such as correction of facial wrinkles and scars, for viscosurgery, such as eye surgery, for viscoprotection, for viscoseparation in post surgical applications, for passive drug delivery, and for viscosupplementation, in particular for the treatment of arthrosis, such as knee arthrosis.

According to an advantageous embodiment, the present invention relates to the use as mentioned above of a compound having the formula (I), wherein k represents an integer varying from 1 to 12.

According to an advantageous embodiment, the present invention relates to the use as mentioned above of a compound of formula (I), wherein k represents an integer varying from 1 to 12, and wherein p is an integer varying from 1 to 6.

The present invention relates to the use as mentioned above of compounds of formula (I), wherein from 2 to 30% of the total $R_i$ groups represent a group of formula (II) or (III), with the proviso that at least one of said $R_i$ groups represents a group of formula (III).

The present invention relates to the use as mentioned above of compounds of formula (I), wherein 8% of the total $R_i$ groups represent a group of formula (II) or (III).

When the $R_i$ group corresponds to a group of formula (II) or (III), it will be hereafter, for simplification of the wording, be designated "modified $R_i$ group".

The present invention relates to the use as mentioned above of compounds of formula (I), wherein from 5 to 100%, preferably from 25 to 100%, and most preferably 50%, of the modified $R_i$ groups represent a group of formula (III).

The present invention relates to the use as defined above of compounds of formula (I), wherein from 0 to 95% of the modified $R_i$ groups represent a group of formula (II).

The present invention relates to the use as mentioned above of compounds of formula (I), wherein from 0 to 28.5% of the total $R_i$ groups represent a group of formula (II).

The present invention relates to the use as defined above of compounds of formula (I), wherein from 0.1 to 30% of the total $R_i$ groups represent a group of formula (III).

According to an advantageous embodiment, the present invention relates to the use as mentioned above of compounds of formula (I), wherein from 0 to 7.6% of the total $R_i$ groups represent a group of formula (II).

The present invention relates to the use as defined above of compounds of formula (I), wherein from 0.4 to 8% of the total $R_i$ groups represent a group of formula (III).

According to an advantageous embodiment, the present invention relates to the use as mentioned above of compounds of formula (I), wherein k represents an integer varying from 1 to 12, and wherein p is an integer varying from 7 to 17.

According to an advantageous embodiment, the present invention relates to the use as mentioned above of compounds of formula (I), wherein k represents an integer varying from 13 to 17, and wherein p is an integer varying from 1 to 6.

According to an advantageous embodiment, the present invention relates to the use as mentioned above of compounds of formula (I), wherein k represents an integer varying from 13 to 17, and wherein p is an integer varying from 7 to 17.

The present invention also relates to the use of a compound having the following formula (I):

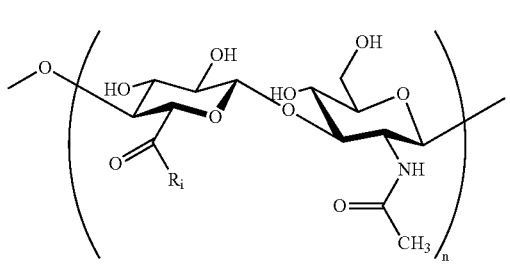

wherein:
n represents an integer varying from 720 to 6 200, preferably from 1 900 to 3 800,
i varies from 1 to n,
$R_i$ represents:
 OH,
 OZ, wherein Z represents any monovalent counterion such as $Na^+$ or $K^+$ or any divalent counterion such as $Ca^{2+}$ or $Mg^{2+}$, and is preferably a monovalent cation,
 or
 a group of the following formula (II):

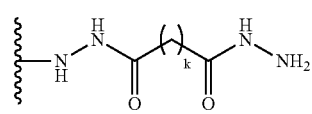

wherein:
 k represents an integer varying from 1 to 17, preferably from 2 to 12, and is in particular equal to or greater than 4,
 or a group of the following formula (III):

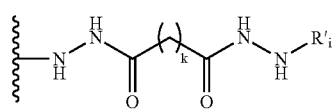

wherein:
 k represents an integer varying from 1 to 17, preferably from 2 to 12, and is in particular equal to or greater than 4,
 $R'_i$ represents a linear or branched alkyl chain comprising p carbon atoms, wherein p is an integer equal to or greater than 7, and preferably is 10,
 with the proviso that k+p is not greater than 28, and preferably not greater than 20,
and wherein at least one $R_i$ group represents a group of formula (III),
for the preparation of a viscoelastic composition.

According to an advantageous embodiment, the invention relates to the use of compounds of formula (I) wherein n represents an integer varying from 720 to 6 250.

According to a more advantageous embodiment, the invention relates to the use of compounds of formula (I) wherein n represents an integer varying from 1 900 to 3 800, or from 2 000 to 3 700.

The present invention also relates to the use of a compound having the following formula (I):

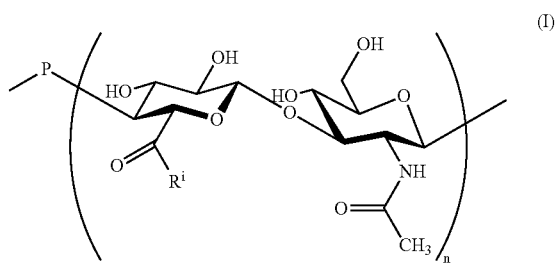

wherein:
n represents an integer varying from 720 to 6 200, preferably from 1 900 to 3 800,
i varies from 1 to n,
$R_i$ represents:
 OH,
 OZ, wherein Z represents any monovalent counterion such as $Na^+$ or $K^+$ or any divalent counterion such as $Ca^{2+}$ or $Mg^{2+}$, and is preferably a monovalent cation,
 or
 a group of the following formula (II):

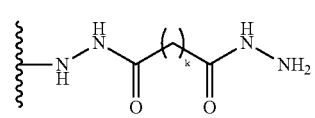

wherein:
 k represents an integer varying from 1 to 17, preferably from 2 to 12, and is in particular equal to or greater than 4,
 or a group of the following formula (III):

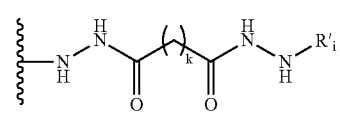

wherein:
 k represents an integer varying from 1 to 17, preferably from 2 to 12, and is in particular equal to or greater than 4,
 $R'_i$ represents a linear or branched alkyl chain comprising p carbon atoms, wherein p is an integer equal to or greater than 7, and preferably is 10,
 with the proviso that k+p is not greater than 28, and preferably not greater than 20,
and wherein at least one $R_i$ group represents a group of formula (III), for the manufacture of a drug for cell culture, tissue engineering, soft tissue augmentation such as correction of facial wrinkles and scars, for viscosurgery, such as eye surgery, for viscoprotection, for viscoseparation in post surgical applications, for passive drug delivery, and for viscosupplementation, in particular for the treatment of arthrosis, such as knee arthrosis.

According to an advantageous embodiment, the invention relates to the use of compounds of formula (I) wherein n represents an integer varying from 720 to 6 250.

According to a more advantageous embodiment, the invention relates to the use of compounds of formula (I) wherein n represents an integer varying from 2 000 to 3 800.

The invention also relates to the use of compounds of formula (I), wherein p is 8, 9, 10, 11, 12, 13, 14, 15, 16 or 17.

The invention also relates to the use of compounds of formula (I), wherein k is 2, 3, 4, 5, 6, 7, 8, 9, 10, 11, 12, 13, 14, 15, 16 or 17.

The invention relates to the use as mentioned above of compounds of formula (I), wherein from 2 to 30% of the total $R_i$ groups represent a group of formula (II) or (III).

Such a substitution degree (2-30%) is an important characteristic of the products of the invention and the physical properties of the resulting fluid are linked to this degree. Such a substitution degree allows preserving the solubility properties and the association of alkyl chains to obtain a homogeneous network wherein the electrostatic repulsions induce the swelling of the gel.

The substitution degree is chosen in such a way that there is a balance in the compounds of the invention between the electrostatic repulsions and the hydrophobic attractions.

The invention relates to the use as mentioned above of compounds of formula (I), wherein 8% of the total $R_i$ groups represent a modified group $R_i$.

Such a preferred substitution degree leads to a control of the crosslinking and allows the association of alkyl chains while maintaining the swelling of the gel.

The invention relates to the use as mentioned above of compounds of formula (I), wherein from 5 to 100%, preferably from 25 to 100%, and most preferably 50%, of the modified $R_i$ groups represent a group of formula (III).

The invention relates to the use as mentioned above of compounds of formula (I), wherein from 0 to 95% of the modified $R_i$ groups represent a group of formula (II).

The invention relates to the use as mentioned above of compounds of formula (I), wherein from 0 to 28.5% of the total $R_i$ groups represent a group of formula (II) as defined above.

The invention relates to the use as mentioned above of compounds of formula (I), wherein from 0.1 to 30% of the total $R_i$ groups represent a group of formula (III).

The invention relates to the use as mentioned above of compounds of formula (I), wherein from 5 to 100% of the modified $R_i$ groups represent a group of formula (III) as defined above, wherein p is 10.

The invention relates to the use as mentioned above of compounds of formula (I), wherein k is equal to or greater than 4.

The invention relates to the use as mentioned above of compounds of formula (I), wherein k is 4.

The invention relates to the use as mentioned above of compounds of formula (I), wherein n is an integer varying from 2 400 to 3 800, and preferably from 2 400 to 3 700.

The above-mentioned compounds of formula (I), wherein n is an integer varying from 2 400 to 3 800, have a molecular weight from about $1 \times 10^6$ to $1.5 \times 10^6$ g.mol$^{-1}$.

The present invention relates to the use of a compound having the following formula (I):

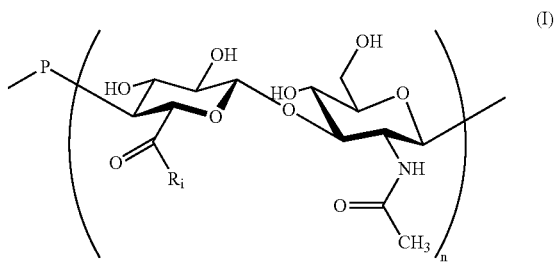

wherein:
n represents an integer varying from 720 to 6 200, preferably from 1 900 to 3 800,
i varies from 1 to n,
$R_i$ represents:
  OH,
  OZ, wherein Z represents any monovalent counterion such as Na$^+$ or K$^+$ or any divalent counterion such as Ca$^{2+}$ or Mg$^{2+}$, and is preferably a monovalent cation, or
  a group of the following formula (II-1):

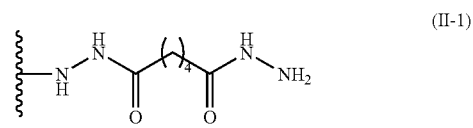

a group of the following formula (III-1):

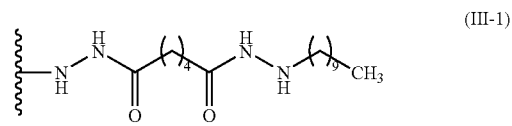

and wherein at least one $R_i$ group represents a group of formula (III-1), for the preparation of a viscoelastic composition.

Advantages of these preferred compounds are the following: a non covalent crosslink by hydrophobic interactions, a good solubility in aqueous solution, good rheological properties and higher performances for viscosupplementation compared to the viscosupplements produced on the market (see experimental part).

The present invention also relates to the use of a compound having the following formula (I):

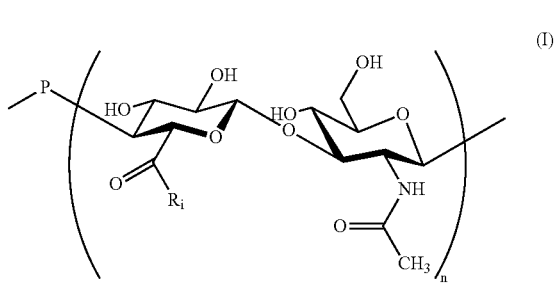

wherein:
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation,
  or
a group of the following formula (II-1):

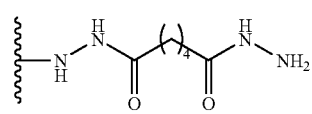

(II-1)

a group of the following formula (III-1):

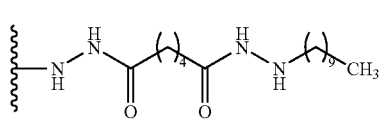

(III-1)

and wherein at least one $R_i$ group represents a group of formula (III-1), for the manufacture of a drug for cell culture, tissue engineering, soft tissue augmentation such as correction of facial wrinkles and scars, for viscosurgery, such as eye surgery, for viscoprotection, for viscoseparation in post surgical applications, for passive drug delivery, and for viscosupplementation, in particular for the treatment of arthrosis, such as knee arthrosis.

The present invention relates to the above-mentioned use of compounds of formula (I), wherein 8% of the total $R_i$ groups represent a group of formula (II-1) or (III-1).

The present invention relates to the above-mentioned use of compounds of formula (I), wherein 5% of the total $R_i$ groups represent a group of formula (III-1), and 3% of the total $R_i$ groups represent a group of formula (II-1).

The use of any of claims 3 to 6, wherein n is an integer varying from 2 400 to 3 800.

These preferred compounds are particularly advantageous as their elastic properties are better than those of Synvisc®, while reducing the amounts of injected compound.

The present invention also relates to a compound having the following formula (I):

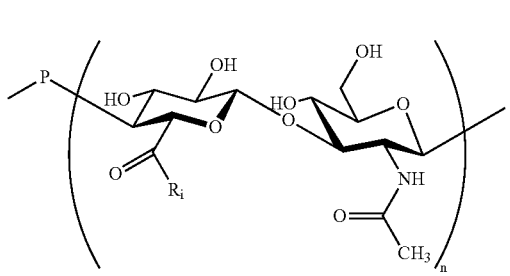

(I)

wherein:
n represents an integer varying from 720 to 6 200, preferably from 1 900 to 3 800, i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation,
  or
a group of the following formula (II):

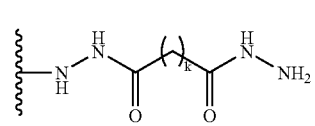

(II)

wherein:
k represents an integer varying from 1 to 17, preferably from 2 to 12, and is in particular equal to or greater than 4,
or a group of the following formula (III'):

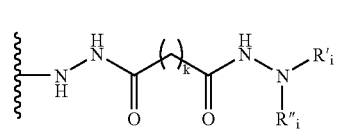

(III')

wherein:
k represents an integer varying from 1 to 17, and is in particular equal to or greater than 4,
$R'_i$ represents a linear or branched alkyl chain comprising p carbon atoms, or a ring comprising p carbon atoms, such as adamantane, wherein p is an integer varying from 1 to 17, and is in particular equal to or greater than 7, and preferably is 10,
$R''_i$ represents H or a linear or branched alkyl chain comprising p' carbon atoms, wherein p' is an integer varying from 1 to 17, and is in particular equal to or greater than 7, and preferably is 10,
with the proviso that k+p+p' is not greater than 28, and preferably not greater than 20,
and wherein at least one $R_i$ group represents a group of formula (III').

The present invention also relates to a compound having the following formula (I):

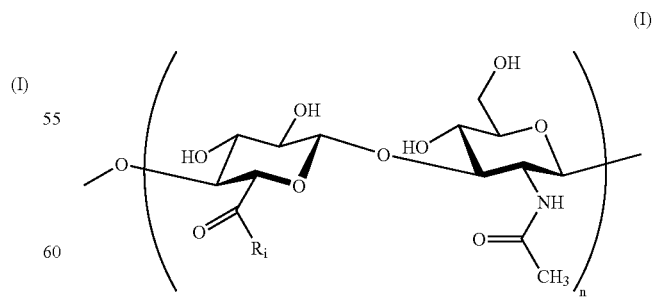

(I)

wherein:
n represents an integer varying from 720 to 6 200, preferably from 1 900 to 3 800,
i varies from 1 to n, $R_i$ represents:
OH,
OZ, wherein Z represents any monovalent counterion such as $Na^+$ or $K^+$ or any divalent counterion such as $Ca^{2+}$ or $Mg^{2+}$, and is preferably a monovalent cation,
or
a group of the following formula (II):

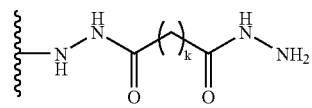
(II)

wherein k represents an integer varying from 1 to 17, preferably from 2 to 12, and is in particular equal to or greater than 4,
or a group of the following formula (III):

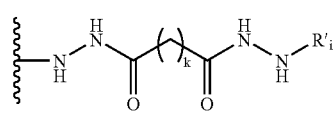
(III)

wherein:
k represents an integer varying from 1 to 17, and is in particular equal to or greater than 4,
$R'_i$ represents a linear or branched alkyl chain comprising p carbon atoms, wherein p is an integer varying from 1 to 17, and is in particular equal to or greater than 7, and preferably is 10,
with the proviso that k+p is not greater than 28, and preferably not greater than 20,
and wherein at least one $R_i$ group represents a group of formula (III).

The compounds of the invention are viscoelastic, amphiphilic as they contain distinct polar (hydrophilic; here the HA backbone) and non polar (hydrophobic; here the alkyl chains) regions.

The compounds of the invention are non-toxic.

The compounds of the invention can be degraded in the body into non-toxic molecules that can be easily eliminated by the organism.

According to an advantageous embodiment, the present invention relates to compounds of formula (I), wherein k represents an integer varying from 1 to 12, and wherein p is an integer varying from 7 to 17.

According to an advantageous embodiment, the present invention relates to compounds of formula (I), wherein k represents an integer varying from 13 to 17, and wherein p is an integer varying from 1 to 6.

According to an advantageous embodiment, the present invention relates to compounds of formula (I), wherein k represents an integer varying from 13 to 17, and wherein p is an integer varying from 7 to 17.

An advantageous compound of the invention is a compound of formula (I) as defined above, wherein from 2 to 30% of the total $R_i$ groups represent a modified group $R_i$ as defined above.

According to an advantageous embodiment, the compound of the invention is a compound of formula (I) as defined above, wherein 8% of the total $R_i$ groups represent a modified group $R_i$ as defined above.

According to an other advantageous embodiment, the compound of the invention is a compound of formula (I) as defined above, wherein from 5 to 100%, preferably from 25 to 100%, and most preferably 50%, of the modified $R_i$ groups represent a group of formula (III) as defined above.

According to an other advantageous embodiment, the compound of the invention is a compound of formula (I) as defined above, wherein from 0 to 95% of the modified $R_i$ groups represent a group of formula (II).

A particularly preferred compound according to the invention is a compound of formula (I) as defined above, wherein from 5 to 100% of the modified $R_i$ groups represent a group of formula (III) as defined above, wherein p is 10.

The present invention relates to a compound of formula (I) as defined above, wherein k is equal to or greater than 4.

The present invention relates to a compound of formula (I) as defined above, wherein k is 4.

The present invention also relates to a compound as defined above, having the following formula (I-2):

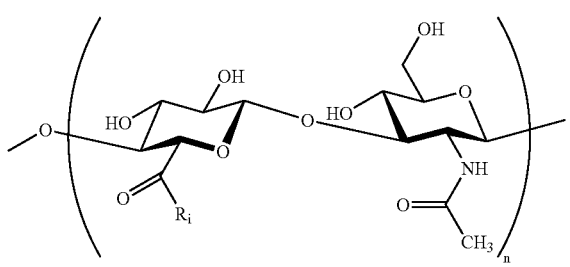
(I-2)

wherein:
n represents an integer varying from 720 to 6 200, preferably from 1 900 to 3 800,
i varies from 1 to n,
$R_i$ represents:
OH,
OZ, wherein Z represents any monovalent counterion such as $Na^+$ or $K^+$ or any divalent counterion such as $Ca^{2+}$ or $Mg^{2+}$, and is preferably a monovalent cation,
or
a group of the following formula (II-2):

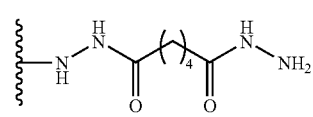
(II-2)

or a group of the following formula (III-2):

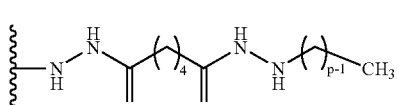
(III-2)

wherein p is an integer equal to or greater than 7, and preferably is 10,
and wherein at least one $R_i$ group represents a group of formula (III-2).

A compound of formula (I-3) corresponds to a compound of formula (I), wherein the group of formula (II) corresponds to a group of formula (II-3), and the group of formula (III) corresponds to a group of formula (III-3).

A group of formula (II-3) corresponds to a group of formula (II).

A group of formula (III-3) corresponds to a group of formula (III), wherein p is 10.

A preferred compound of the invention has the following formula (I-4):

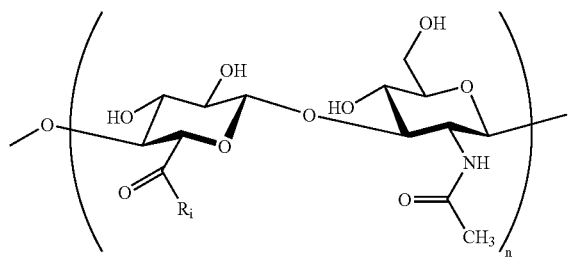

wherein:
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation, or
a group of the following formula (II-1):

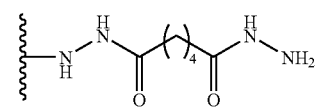

or a group of the following formula (III-1):

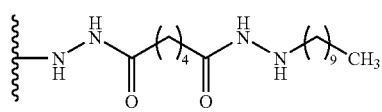

and wherein at least one $R_i$ group represents a group of formula (III-1).

A compound of formula (I-4) corresponds to a compound of formula (I), wherein the group of formula (II) corresponds to a group of formula (II-1), and the group of formula (III) corresponds to a group of formula (III-1).

A compound of formula (I-2) corresponds to a compound of formula (I), wherein the group of formula (II) corresponds to a group of formula (II-2), and the group of formula (III) corresponds to a group of formula (III-2).

A group of formula (II-2) corresponds to a group of formula (II), wherein k is 4.

A group of formula (III-2) corresponds to a group of formula (III), wherein k is 4.

The present invention relates to a compound having the following formula (I-3):

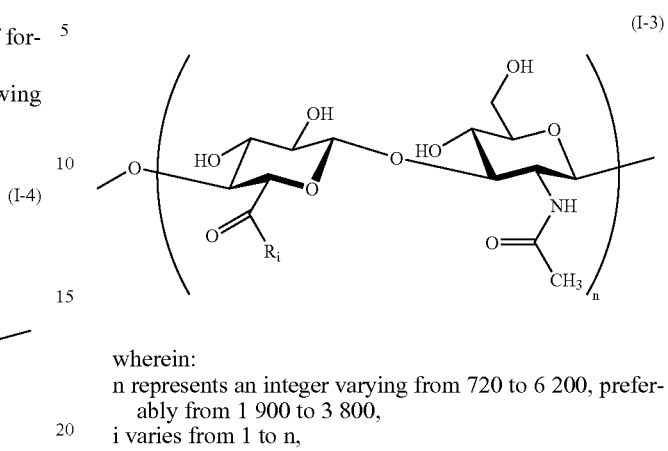

wherein:
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation, or
a group of the following formula (II-3):

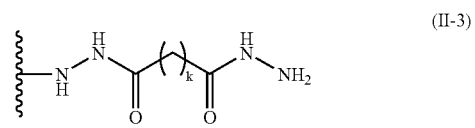

or a group of the following formula (III-3):

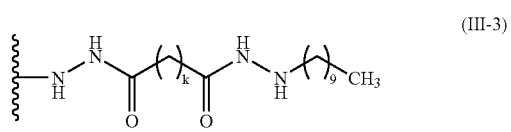

wherein k is equal to or greater than 4,
and wherein at least one $R_i$ group represents a group of formula (III-3).

A group of formula (II-1) corresponds to a group of formula (II), wherein k is 4 and p is 10.

A group of formula (III-1) corresponds to a group of formula (III), wherein k is 4 and p is 10.

Another preferred compound of the invention has the following formula (I-5):

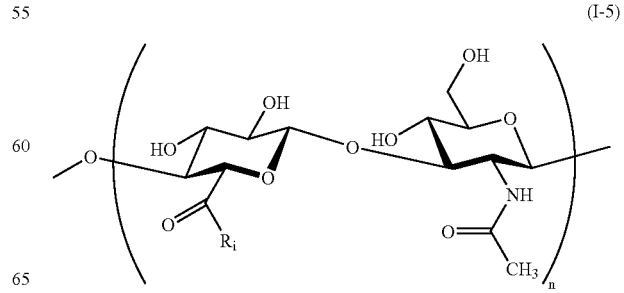

wherein:
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation, or
  a group of the following formula (II-1):

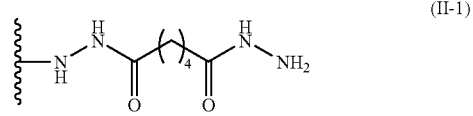

a group of the following formula (III-1):

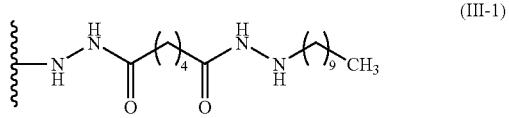

and wherein from 2 to 30% of the total $R_i$ groups represent a group of formula (III-1).

A compound of formula (I-5) corresponds to a compound of formula (I), wherein the group of formula (II) corresponds to a group of formula (II-1), and the group of formula (III) corresponds to a group of formula (III-1), and wherein from 2 to 30% of the total $R_i$ groups represent a group of formula (III-1).

According to an advantageous embodiment, the present invention relates to a compound of formula (I-5) as mentioned above, wherein 8% of the total $R_i$ groups represent a modified group $R_i$, wherein k is 4 and p is 10.

According to an advantageous embodiment, the present invention relates to a compound of formula (I-5) as mentioned above, wherein from 5 to 100% of the modified $R_i$ groups, wherein k is 4 and p is 10, represent a group of formula (III-1).

An advantageous compound according to the present invention is a compound of formula (I-4) or (I-5) as defined above, wherein 5% of the total $R_i$ groups represent a group of formula (III-1), and wherein 3% of the total $R_i$ groups represent a group of formula (II-1).

The present invention relates to a compound of formula (I) as defined above, wherein n is an integer varying from 2 400 to 3 700.

It is interesting to use a higher molecular weight (such in this range) because the Theological parameters are higher; it is demonstrated when the properties of HA300 (compounds of the invention with a molecular weight of 300,000 g.mol$^{-1}$) and HA 1500 (compounds of the invention with a molecular weight of 1,500,000 g.mol$^{-1}$) are compared (see FIGS. 2 and 4).

The compounds of the invention of formula (I) as mentioned above are particularly advantageous, as they are obtained without a process of chemical crosslinking: thus, they can be filtered contrary to Synvisc®, which is chemically crosslinked. Furthermore, they present the property of maintaining their viscoelastic properties during the dilution with a buffer solution (see the experimental part).

The present invention also relates to a composition comprising a mixture of compounds of formula (I) as defined above.

Said mixture can contain compounds having the same formula (I), that is to say compounds of formula (I) wherein n is identical, and wherein each $R_i$ in each motif "i" is identical or compounds of formula (I) wherein n is identical, and wherein each $R_i$ in each motif "i" is not identical.

Said mixture can also contain compounds not having the same formula (I), that is to say compounds of formula (I) wherein n can be different, and/or wherein each $R_i$ in each motif "i" is not identical.

The present invention also relates to a composition comprising a mixture of hyaluronic acid and of the compound of formula (I) as defined above.

Preferably, the present invention relates to a composition comprising a mixture of hyaluronic acid or of its salt forms having a molecular weight of about 400,000 to $2.7 \times 10^6$ g.mol$^{-1}$ and of the compound of formula (I) as defined above, said hyaluronic acid corresponding to non-modified natural hyaluronic acid.

According to an advantageous embodiment, said composition as defined above comprises from 1 to 99% of hyaluronic acid and from 1 to 99%, preferably from 50 to 99% of the compound of formula (I) as defined above.

The present invention also relates to a pharmaceutical composition, comprising a compound of formula (I) as defined above, in association with a pharmaceutically acceptable carrier.

The derivatives of the invention may be adapted for drug delivery but also for many other applications in domains other than pharmaceutical, such as cosmetic and medical.

Examples of such a pharmaceutically acceptable carrier are: cyclodextrins (α, β or γ).

The cyclodextrins are particularly appropriate in the present invention as they reduce the viscosity of the compound of the invention, which makes the injection of said compound easier. More precisely, the hydrophobic interactions are disrupted in contact of cyclodextrin, because the hydrophobic chains will be encapsulated into the cavity of the cyclodextrin and thus masked.

The addition of cyclodextrins for the injection of the compound of the invention facilitates the flow of said compound in the organism.

After the injection of the pharmaceutical composition, as the interactions between the cyclodextrins and the compound of the invention are weak After the injection, the cyclodextrins diffuse by dilution in the organism and also because of the competitive hydrophobic interaction with molecules in-situ, such as lipids.

The interactions between alkyl chains and CD are reversible.

Said pharmaceutical compositions are not toxic.

In the above-mentioned pharmaceutical compositions, the amount of the compound of formula (I) according to the invention varies from about 1 to about 30 g.L$^{-1}$, and is preferably about 10 g.L$^{-1}$.

Furthermore, the pharmaceutical compositions of the invention are in the form of solution presenting gel-like properties and can be more easily injected with a syringe.

The present invention also relates to a composition, in particular a pharmaceutical composition, comprising a compound of formula (I) as defined above, in association with an anionic surfactant, such as sodium octyl sulphate, sodium decyl sulphate, sodium dodecyl sulphate, and sodium tetradecyl sulphate.

The present invention also relates to a process for the preparation of compounds of formula (I):

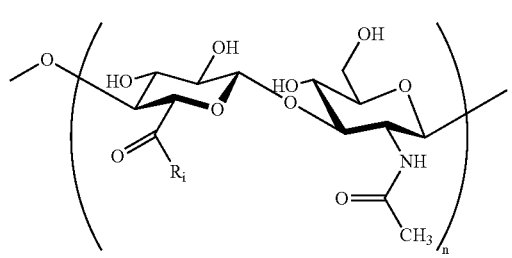

(I)

wherein
n represents an integer varying from 720 to 6 200, preferably from 1 900 to 3 800,
i varies from 1 to n,
$R_i$ represents:
  OH,
  OZ, wherein Z represents any monovalent counterion such as $Na^+$ or $K^+$ or any divalent counterion such as $Ca^{2+}$ or $Mg^{2+}$, and is preferably a monovalent cation,
  or
  a group of the following formula (II):

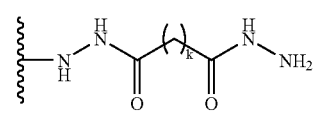

(II)

wherein:
  k represents an integer varying from 1 to 17, preferably from 2 to 12, and is in particular equal to or greater than 4,
  or a group of the following formula (III):

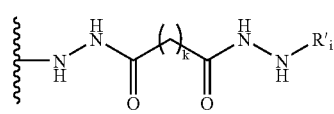

(III)

wherein:
  k represents an integer varying from 1 to 17, preferably from 2 to 12, and is in particular equal to or greater than 4,
  $R'_i$ represents a linear or branched alkyl chain comprising p carbon atoms, wherein p is an integer varying from 1 to 17, preferably from 3 to 16, and is in particular equal to or greater than 7, and preferably is 10,
  with the proviso that k+p is not greater than 28, and preferably not greater than 20,
and wherein at least one $R_i$ group represents a group of formula (III), characterized in that it comprises the following steps:
reacting hyaluronic acid of formula (A):

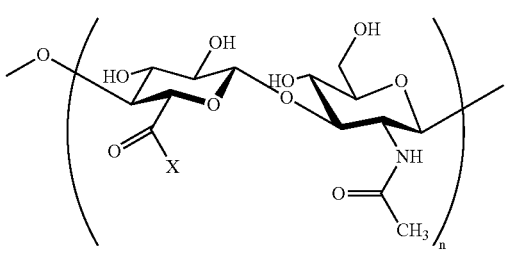

(A)

wherein:
X is OH or OZ, wherein Z represents any monovalent counterion such as $Na^+$ or $K^+$ or any divalent counterion such as $Ca^{2+}$ or $Mg^{2+}$, and is preferably a monovalent cation,
n represents an integer varying from 720 to 6 200, preferably from 1 900 to 3 800,
in the presence of a water-soluble coupling agent, such as a water-soluble carbodiimide such as EDC,
with a dihydrazide of formula (B):

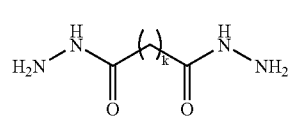

(B)

wherein k represents an integer varying from 1 to 17, preferably from 2 to 12, and is in particular equal to or greater than 4,
to obtain a compound of formula (C):

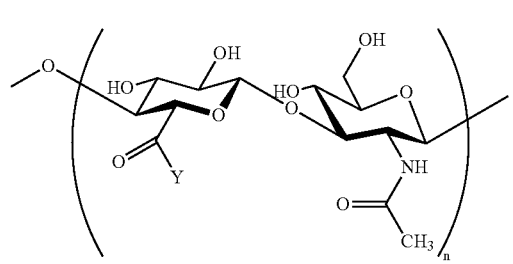

(C)

wherein Y is
  OH or
  OZ, Z being such as defined above, or
  a group of formula (D):

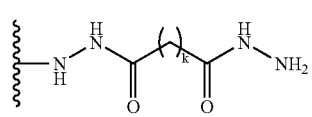

(D)

k being as defined above,
wherein at least one Y group represents a group of formula (D),
and reacting the compound of formula (C) in the presence of a reducing agent, such as $NaCNBH_3$, $NaBH_4$ $Pic-BH_3$ and $Pyr-BH_3$ with an aldehyde comprising from 1 to 17 carbon atoms, preferably from 3 to 16, in particular comprising at least 7 carbon atoms, and preferably comprising 10 carbon atoms, to obtain a compound of formula (I) as defined above.

The present invention also relates to a product such as obtained according to the process such as defined above.

The use of a reducing agent improves the yield of the reaction between aldehyde and hydrazide, when compared to the same reaction without reducing agent, as said reducing agent stabilises the hydrazone bond.

By carrying out the same process without said reducing agent, it is not possible to obtain the products of the invention: it leads only to the obtaining of hydrazone in very small amounts.

According to an advantageous embodiment, the invention relates to the preparation process of compounds of formula (I) wherein n represents an integer varying from 720 to 6 250.

According to a more advantageous embodiment, the invention relates to the preparation process of compounds of formula (I) wherein n represents an integer varying from 2 000 to 3 800.

The present invention also relates to a process for the preparation of compounds of formula (I):

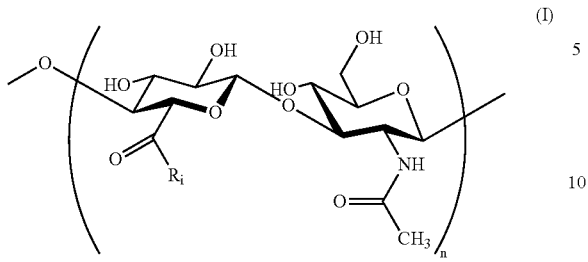

wherein:
n represents an integer varying from 720 to 6 200, preferably from 1 900 to 3 800,
i varies from 1 to n,
$R_i$ represents:
OH,
OZ, wherein Z represents any monovalent counterion such as $Na^+$ or $K^+$ or any divalent counterion such as $Ca^{2+}$ or $Mg^{2+}$, and is preferably a monovalent cation, or
a group of the following formula (II):

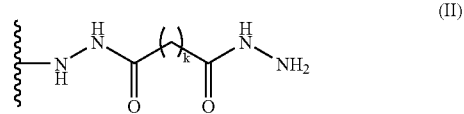

wherein k represents an integer varying from 1 to 17,
or a group of the following formula (III):

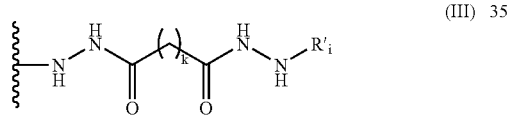

wherein:
k represents an integer varying from 1 to 17,
$R'_i$ represents a linear or branched alkyl chain comprising p carbon atoms, wherein p is an integer varying from 1 to 6,
with the proviso that k+p is not greater than 20,
and wherein at least one $R_i$ group represents a group of formula (III), characterized in that it comprises the following steps:
reacting hyaluronic acid of formula (A):

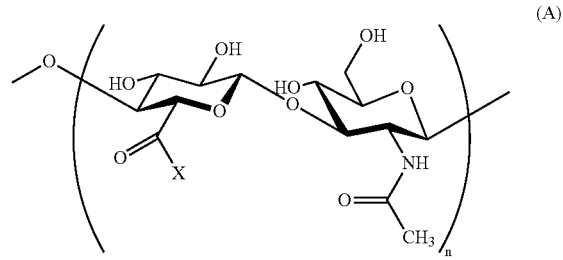

wherein:
X is OH or OZ, wherein Z represents any monovalent counterion such as $Na^+$ or $K^+$ or any divalent counterion such as $Ca^{2+}$ or $Mg^{2+}$, and is preferably a monovalent cation, n represents an integer varying from 720 to 6 200, preferably from 1 900 to 3 800,
in the presence of a water-soluble coupling agent, such as a water-soluble carbodiimide such as EDC,
with a dihydrazide of formula (B):

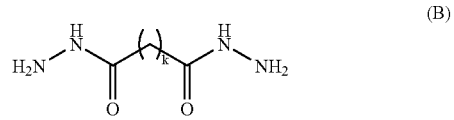

wherein k represents an integer varying from 1 to 17,
to obtain a compound of formula (C):

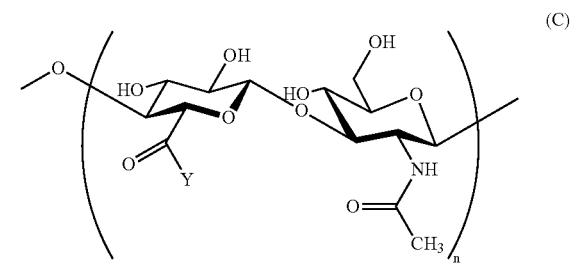

wherein Y is
OH or
OZ, Z being such as defined above, or
a group of formula (D):

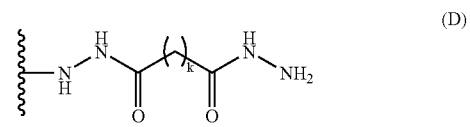

k being as defined above,
wherein at least one Y group represents a group of formula (D),
and reacting the compound of formula (C) in the presence of a reducing agent with an aldehyde comprising from 1 to 6 carbon atoms, to obtain a compound of formula (I) as defined above.

The present invention also relates to a product such as obtained according to the process such as defined above.

The present invention also relates to a process for the preparation of compounds of formula (I):

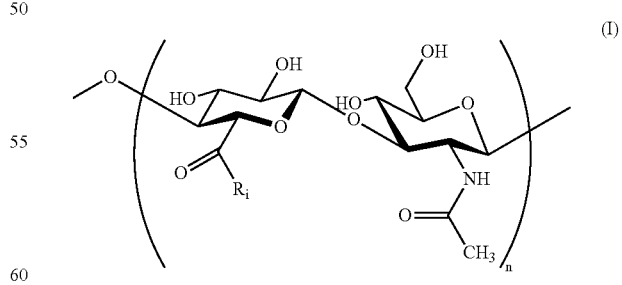

wherein:
n represents an integer varying from 720 to 6 200, preferably from 1 900 to 3 800,
i varies from 1 to n,
$R_i$ represents:
OH, OZ, wherein Z represents any monovalent counterion such as Na$^+$ or K$^+$ or any divalent counterion such as Ca$^{2+}$ or Mg$^{2+}$, and is preferably a monovalent cation,
or
a group of the following formula (II):

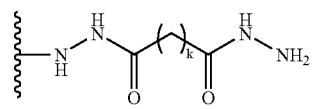

(II)

wherein k represents an integer varying from 1 to 17, preferably from 2 to 12, and is in particular equal to or greater than 4,
or a group of the following formula (III):

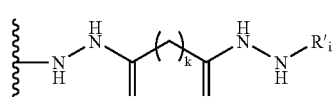

(III)

wherein:
k represents an integer varying from 1 to 17, preferably from 2 to 12, and is in particular equal to or greater than 4,
R$'_i$ represents a linear or branched alkyl chain comprising p carbon atoms, wherein p is an integer equal to or greater than 7, and particularly varying from 7 to 17, and preferably is 10,
with the proviso that k+p is not greater than 28,
and wherein at least one R$_i$ group represents a group of formula (III), characterized in that it comprises the following steps:
reacting hyaluronic acid of formula (A):

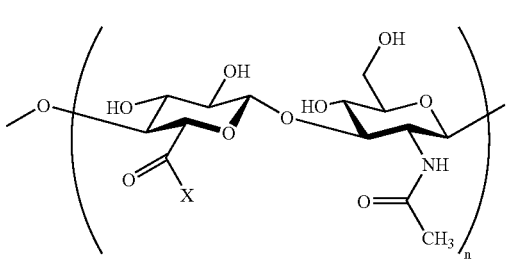

(A)

wherein:
X is OH or OZ, wherein Z represents any monovalent counterion such as Na$^+$ or K$^+$ or any divalent counterion such as Ca$^{2+}$ or Mg$^{2+}$, and is preferably a monovalent cation,
n represents an integer varying from 720 to 6 200, preferably from 1 900 to 3 800,
in the presence of a water-soluble coupling agent, such as a water-soluble carbodiimide such as EDC,
with a dihydrazide of formula (B):

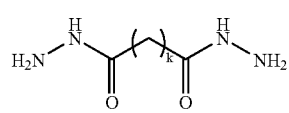

(B)

wherein k represents an integer varying from 1 to 17, preferably from 2 to 12, and is in particular equal to or greater than 4, to obtain a compound of formula (C):

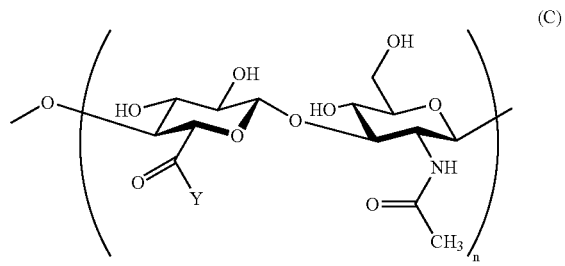

(C)

wherein Y is
OH or
OZ, Z being such as defined above, or
a group of formula (D):

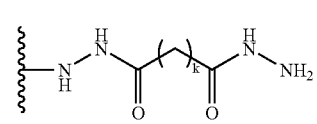

(D)

k being as defined above,
wherein at least one Y group represents a group of formula (D),
and reacting the compound of formula (C) in the presence of a reducing agent with an aldehyde comprising at least 7 carbon atoms, and preferably comprising 10 carbon atoms, to obtain a compound of formula (I) as defined above.

The present invention also relates to a product such as obtained according to the process such as defined above.

The present invention also relates to a process for the preparation of compounds of formula (I-5):

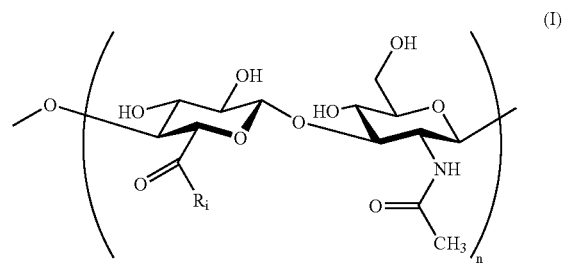

(I)

wherein:
n represents an integer varying from 720 to 6 200, preferably from 1 900 to 3 800,
i varies from 1 to n,
R$_i$ represents:
OH,
OZ, wherein Z represents any monovalent counterion such as Na$^+$ or K$^+$ or any divalent counterion such as Ca$^{2+}$ or Mg$^{2+}$, and is preferably a monovalent cation,
or
a group of the following formula (II-1):

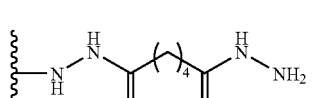

(II-1)

a group of the following formula (III-1):

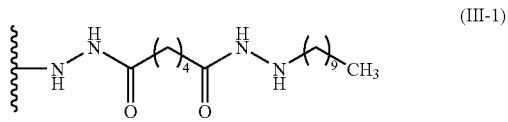

and wherein from 2 to 30% of the total $R_i$ groups represent a group of formula (III-1),
characterized in that it comprises the following steps:
reacting hyaluronic acid of formula (A):

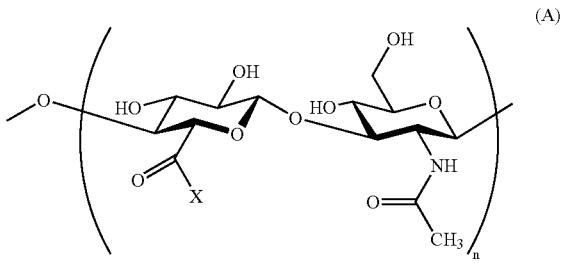

wherein:
X is OH or OZ, wherein Z represents any monovalent counterion such as $Na^+$ or $K^+$ or any divalent counterion such as $Ca^{2+}$ or $Mg^{2+}$, and is preferably a monovalent cation,
n represents an integer varying from 720 to 6 200, preferably from 1 900 to 3 800,
in the presence of a water-soluble carbodiimide such as EDC,
with a dihydrazide of formula (B-1):

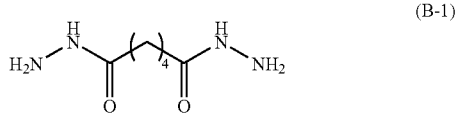

to obtain a compound of formula (C-1):

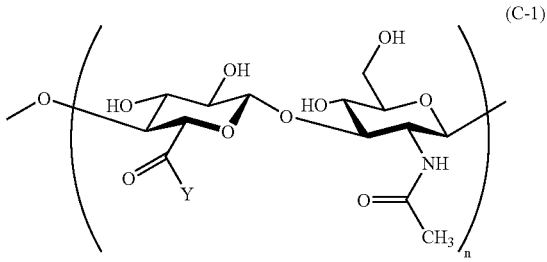

wherein Y is
OH or
OZ, Z being such as defined above, or
a group of formula (D-1):

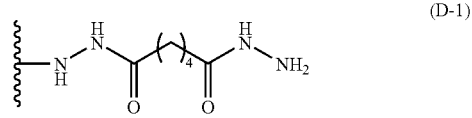

wherein at least one Y group represents a group of formula (D-1),
and reacting the compound of formula (C-1) in the presence of a reducing agent with an aldehyde comprising 10 carbon atoms, to obtain a compound of formula (I-5) as defined above.

The present invention also relates to a product such as obtained according to the process such as defined above.

The present invention also relates to a preparation process of a composition comprising a mixture of compounds of formula (I) as defined above, by mixing together compounds of formula (I) as defined above.

The present invention also relates to a preparation process of a composition comprising a mixture of hyaluronic acid and of the compound of formula (I) as defined above, by mixing a solution of linear hyaluronic acid (natural hyaluronic acid and its salt forms which is not modified) with a solution of compounds of formula (I) as defined above.

EXPERIMENTAL PART

Figure 1:
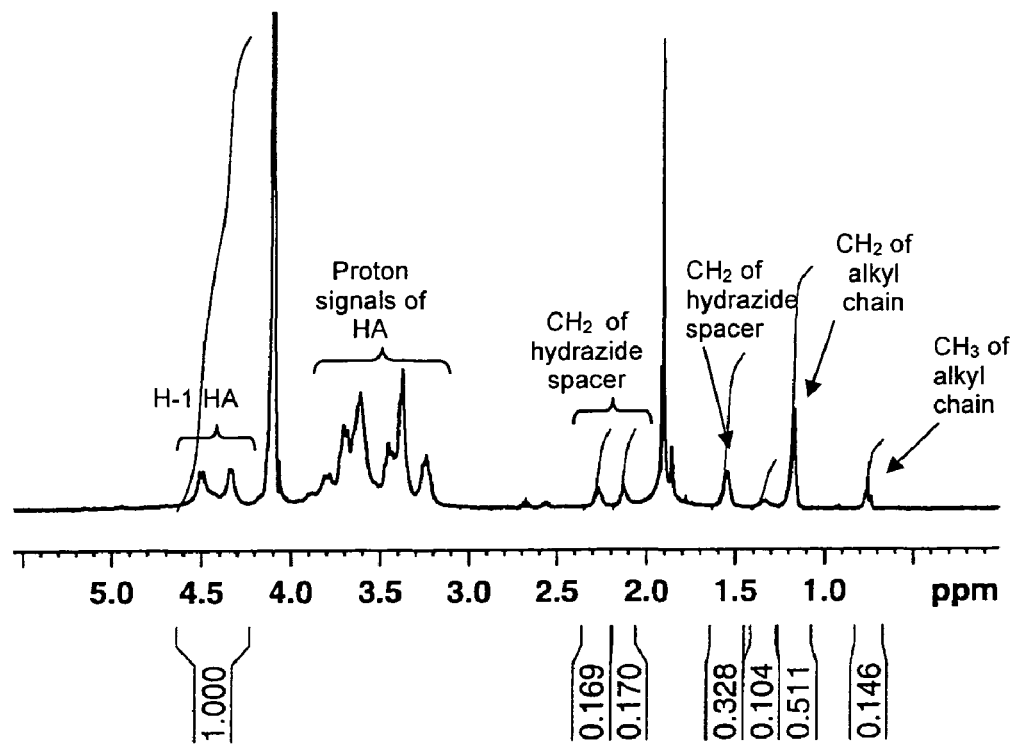
FIG. 1. $^1H$ NMR spectrum (400 MHz, 80° C., 6 mg.mL$^{-1}$ in $D_2O$ (HOD signal at 4.11 ppm)) of a compound of formula (I) with C-10 alkyl chains (p=10) and wherein 5% of the total groups $R_i$ are groups of formula (III) as defined above with k=4 and p=10 (DS=0.05).

Materials.

The hyaluronic acid used as raw material in the present invention, is based on the pathway previously described with a non GMO strain, the glucose as carbon source, wheat proteins as nitrogen source, and purification process based on filtration processes and alcoholic precipitation and drying. This polysaccharide has become an attractive building block for the development of new biocompatible materials with many applications in viscosupplementation (reducing pain and re-establishing functions in arthritic joints), tissue engineering (3 D-cell culture biosorbable scaffolds) and drug delivery (Lapčik Jr., L.; Lapčik, L.; De Smedt, S.; Demeester, J. *Chem. Rev.* 1998, 98, 2663; *New Frontiers in Medical sciences: Redefining Hyaluronan*; Abatangelo G., Weigel P. H. Eds.; Elsevier; 2000).

This bacterial sodium hyaluronate was used in this work. The molecular weight distribution (w(M)) and the weight-average molecular weight ($M_w$) were determined by size exclusion chromatography using triple detection equipment from solutions at a concentration of $5 \times 10^{-4}$ g/mL in 0.1 M $NaNO_3$. The polydispersity of the samples is $M_w/M_n$~1.5. The weight-average molecular weights were determined to be $1.5 \times 10^6$ g/mol and $3 \times 10^5$ g/mol. In the following, these samples are referred to HA 1500 and HA 300, respectively. The protein content was determined to be less than 0.1% by weight. The aldehydic chains (1-decanal or 1-dodecanal) and all other chemicals were purchased from Fluka (Buchs, Switzerland).

NMR Spectroscopy.

$^1$H NMR experiments were performed using a DRX400 spectrometer produced by Bruker operating at 400 MHz. $^1$H NMR spectra were collected using 16K data points. Deuterium oxide was obtained from SDS (Vitry, France).

Synthesis of Compounds of Formula (I)

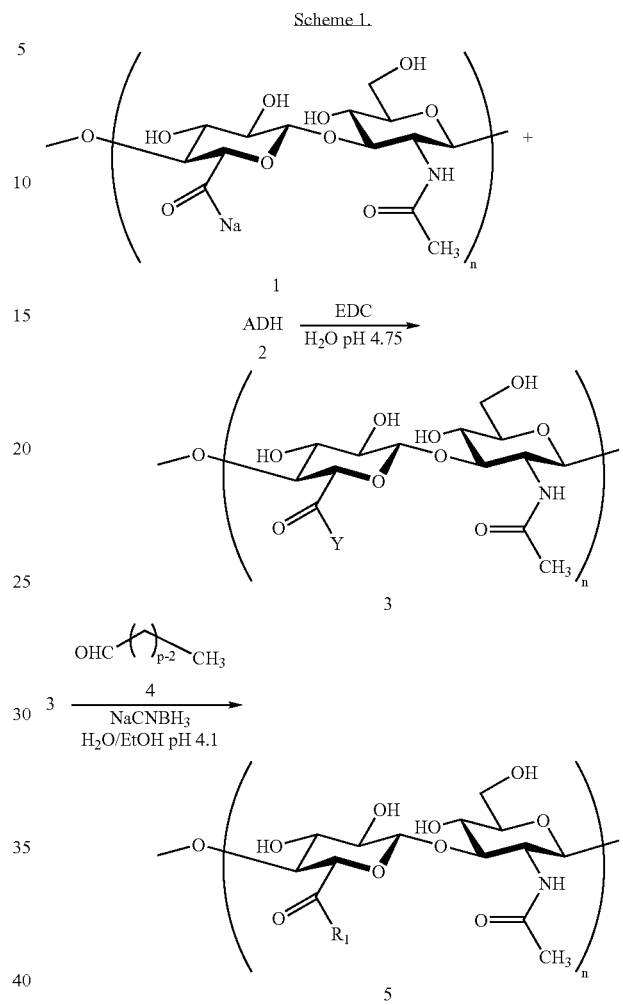

HA-ADH 3 (Compound (C-1) of the Invention with k=4)

HA 300 (4 g, 9.97 mmol) (compound (A) with n=750) was dissolved in water to a concentration of 4 g/L. To this solution, adipic dihydrazide (17.3 g, 99.7 mmol) (compound (B-1)) was added. The pH of the reaction was then adjusted to 4.75±0.05 using 0.1 N HCl. Next, an aqueous solution of 1-ethyl-3-(3-(dimethylamino)propyl) carbodiimide (EDC) (0.287 g, 1.49 mmol) was added slowly to the mixture. The pH of the reaction mixture was maintained at 4.75±0.05 by addition of 0.1 N HCl. The reaction was allowed to proceed at room temperature until no further change in pH was observed (i.e 4 hours). The pH of the reaction was then adjusted to 7.5 with 0.1 N NaOH. After addition of NaCl at a concentration of 0.5 M, the modified HA was precipitated with EtOH in the proportion EtOH/$H_2O$ around 3/2 (v/v). The precipitate was washed with ethanol and then filtered to give HA-ADH (3.48 g, 85%). The chemical integrity and purity of the final product were checked by $^1$H NMR. Digital integration of the NMR signals arising from the anomeric protons of HA and methylene protons of ADH gave a substitution degree of 0.08.

Alkylated HA 5a (Compounds of Formula (I) According to the Invention with k=4; p=10)

To a solution of HA-ADH 3 (0.6 g, 1.46 mmol) in a water (144 mL), EtOH (82 mL) was added. The pH of the solution was then adjusted to 5.1±0.5 by the dropwise addition of a 0.1 M aqueous HCl solution. The aldehydic chain (1-decanal) (0.015 g, 0.096 mmol) (p=10) was then added, followed by a solution of $NaCNBH_3$ (reducing agent) (0.21 g, 2.84 mmol) in water (2 mL). After stirring for 24 h at room temperature, the pH of the reaction was then adjusted to 7.5 with aqueous 0.1 N NaOH. After addition of NaCl at a concentration of 0.5 M, the modified HA was precipitated with EtOH in the proportion $EtOH/H_2O$ around 3/2 (v/v). The precipitate was washed with ethanol and then, was filtered to give HA-5C10, a compound of formula (I) with n=750, and 5% of the total $R_i$ groups representing a group of formula (III) with k=4 and p=10.

The polymers are designated as HA-xCy where x is the number of groups $R_i$ of formula (III) for 100 groups $R_i$, and y is the number of carbon of the pendant alkyl chain (p).

The above-mentioned synthesis could also be carried out by using other types of aldehyde chains.

An alternative method of synthesis of alkylated HA 5a (compounds of formula (I) according to the invention with k=4; p=10) is as follows:

HA600 (1 g, 2.49 mmol) (compound (A) with n=1500) was dissolved in water to a concentration of 2 g/L. Adipic dihydrazide (0.432 g, 2.49 mmol) (compound (B-1)) was added to this solution. After 15 h of stirring, the solution was filtered through a 0.22 μm membrane. The pH of the reaction was then adjusted to 4.75±0.05 using 0.5 M HCl. Next, an aqueous solution of 1-ethyl-3(3-dimethylaminopropyl)carbodiimide (EDC) (0.071 g, 0.37 mmol) was added slowly to the mixture. The pH of the reaction mixture was maintained at 4.75±0.05 by addition of 0.5 M HCl. The reaction was allowed to proceed at room temperature until no further change in pH was observed (i.e. 4 hours). The pH of the reaction was then adjusted to 7.5 with 0.5 M NaOH. The product was purified by ultrafiltration using a Millipore membrane (pore size 100.000 MW). After purification by ten times the initial volume, the conductivity of the permeate solution was measured and it was checked that it was that of the deionised water (~5 μS). To the solution of modified HA obtained after ultrafiltration (500 mL), EtOH (333 mL) was added. The pH of the solution was then adjusted to 5.10±0.05 by the dropwise addition of a 0.1 M aqueous HCl solution. The aldehydic chain (1-decanal) (0.025 g, 0.160 mmol) (p=10) was then added, followed by a solution of 2-picoline borane complex ($PicBH_3$) (0.130 g, 1.215 mmol) in ethanol (1 mL). After stirring for 24 h at room temperature, the pH of the reaction was adjusted to 7.5 with aqueous 0.1 M NaOH. After addition of NaCl at a concentration of 0.5 M, the modified HA was precipitated with EtOH in the $EtOH/H_2O$ proportion of 3/2 (v/v). The precipitate was washed with ethanol, and then filtered to give HA-5C10, a compound of formula (I) with n=1500, and 5% of the Ri groups representing a group of formula (III) with k=4 and p=10.

The above-mentioned synthesis could also be carried out by using other types of aldehyde chains or reducing agents ($NaCNBH_3$, $NaBH_4$, ...).

RESULTS

Synthesis and Characterization of Alkylated HA Derivatives.

Reaction of HA 1 (compound (A)) with 10 molar equivalents of adipic dihydrazide (ADH) 2 (compound (B-1)) and 0.15 molar equivalent of 1-ethyl-3-[3-(dimethylamino)propyl]-carbodiimide (EDC) in water at pH 4.75±0.05 allowed to obtain a highly pure HA-ADH derivative 3 (Scheme 1). The degree of substitution (DS) determined from $^1H$ NMR was found equal to 0.08, as expected. Indeed, a low DS value for HA-ADH (DS≦0.1) was targeted in order to preserve the unique viscoelastic properties observed with the native polymer and also to maintain a high charge density on the HA backbone, which is at the origin of the water-solubility of the polymer. Then, HA-ADH 3 was reacted with different aldehydic chains 4 with 10 and 12 carbon atoms (or other chain structure) in the presence of sodium cyanoborohydride in a water/ethanol mixture at pH 5.1±0.5 (Scheme 1).

The addition of a reducing agent, in the present case, allowed to significantly increase the yield of reaction due to the stabilization of hydrazone bond. Indeed, under such conditions, the coupling reaction was shown to be quasi-quantitative. The chemical integrity and purity of the final products (I) were checked by high-resolution $^1H$ NMR. The NMR analysis was performed in $D_2O$ and demonstrated that the alkylated HA derivatives was free of any by-product. As an example, FIG. 1 shows the NMR spectrum of a HA sample with C-10 chains (p=10) where digital integration of the NMR signals arising from the anomeric protons of HA and the protons of the $CH_3$ group of the chain gives a substitution degree (DS=x/100) of 0.05.

The ionic concentration of the solvent as well as the temperature has some effect on this behavior in relation with the balance between electrostatic repulsions and hydrophobic attractions characterizing these amphiphilic systems.

HA-5C10 is a compound of formula (I), wherein 5% of the total $R_i$ groups representing a group of formula (III) with k=4 and p=10, and 3% of the total $R_i$ groups representing a group of formula (II) with k=4.

HA-4C12 is a compound of formula (I), wherein 4% of the total $R_i$ groups representing a group of formula (III) with k=4 and p=12 and 4% of the total $R_i$ groups representing a group of formula (II) with k=4.

RHEOLOGY

Rheological Experiments.

Oscillatory experiments were performed with a cone-plate rheometer (AR1000 from TA Instruments). All the dynamic rheological data (elastic modulus G', loss modulus G", complex viscosity η*) were checked as a function of strain amplitude to ensure that the measurements were performed in the linear viscoelastic region; then, they were examined as a function of the frequency (ω in Hz). Steady shear flow experiments (η, viscosity as a function of the shear rate γ) for polymer concentrations higher than 3 g/L were carried out with the same cone-plate rheometer. The cones used have a diameter of 4 cm and an angle of 3°59' or a diameter of 6 cm and an angle of 10 depending on the viscosity of the systems to measure. Most of experiments were carried out at 25° C. or 37° C., with a film of silicone to avoid solvent evaporation. Solutions of natural HA and alkylated HA derivatives according to the invention were prepared by dissolving them in the aqueous solvent (0.1 M NaCl or the buffer consisting of: 8.5 g/L NaCl, 0.05 g/L $NaH_2PO_4$, 0.6 g/L $Na_2HPO_4$). After stirring overnight, the samples were kept in the refrigerator for one day prior to characterization.

I—Flow Curves at 25° C. Comparison with Data from Literature

Figure 2:
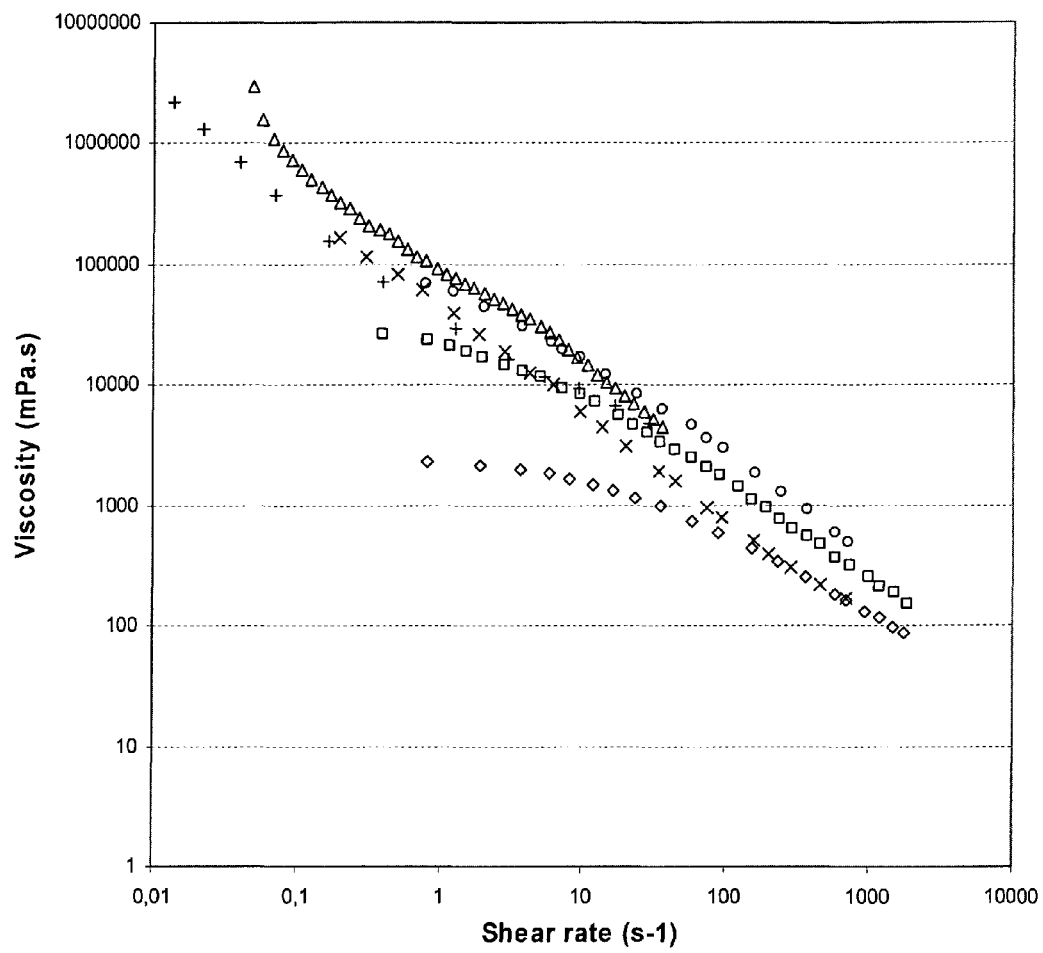
FIG. 2. Flow experiments giving the viscosity (mPa·s) as a function of the shear rate for commercial HA (values taken from a commercial sheet): Arthrum® (○); Orthovisc® (□); Supartz®/Adant® (◇); Synvisc® (x); and the HA derivatives of the invention of formula (I): HA-5C10 of molecular weight of 300,000 g.mol$^{-1}$ (+) and 1,500,000 g.mol$^{-1}$ (Δ) in NaCl 0.1M at 25° C.

The viscosity as a function of the shear rate was drawn for two of our polymers and compared with data taken from a commercial sheet for different commercial products (FIG. 2). In FIG. 2, solvents are those adopted by the different companies. For the modified HA (5-C10 Mw=0.3×$10^6$ and 5-C10

Mw=1.5×10$^6$), solvent is 0.1 M NaCl and the measurements are performed at 25° C. All the samples are at 10 g/L but Arthrum® is at 20 g/L.

From this comparison figure, it is clear that the viscosity of the products of the invention is higher than the majority of the commercial samples, and, especially, the viscosity of the HA derivative of the invention HA-5C10 with Mw=1.5×10$^6$ g/mol is higher than the viscosity of the most effective product considered at the same polymer concentration 10 g/L. It is even clearer when compared with Arthrum® prepared at a double concentration.

II—Flow Curves at 37° C. in Phosphate-NaCl Buffer

Figure 3:
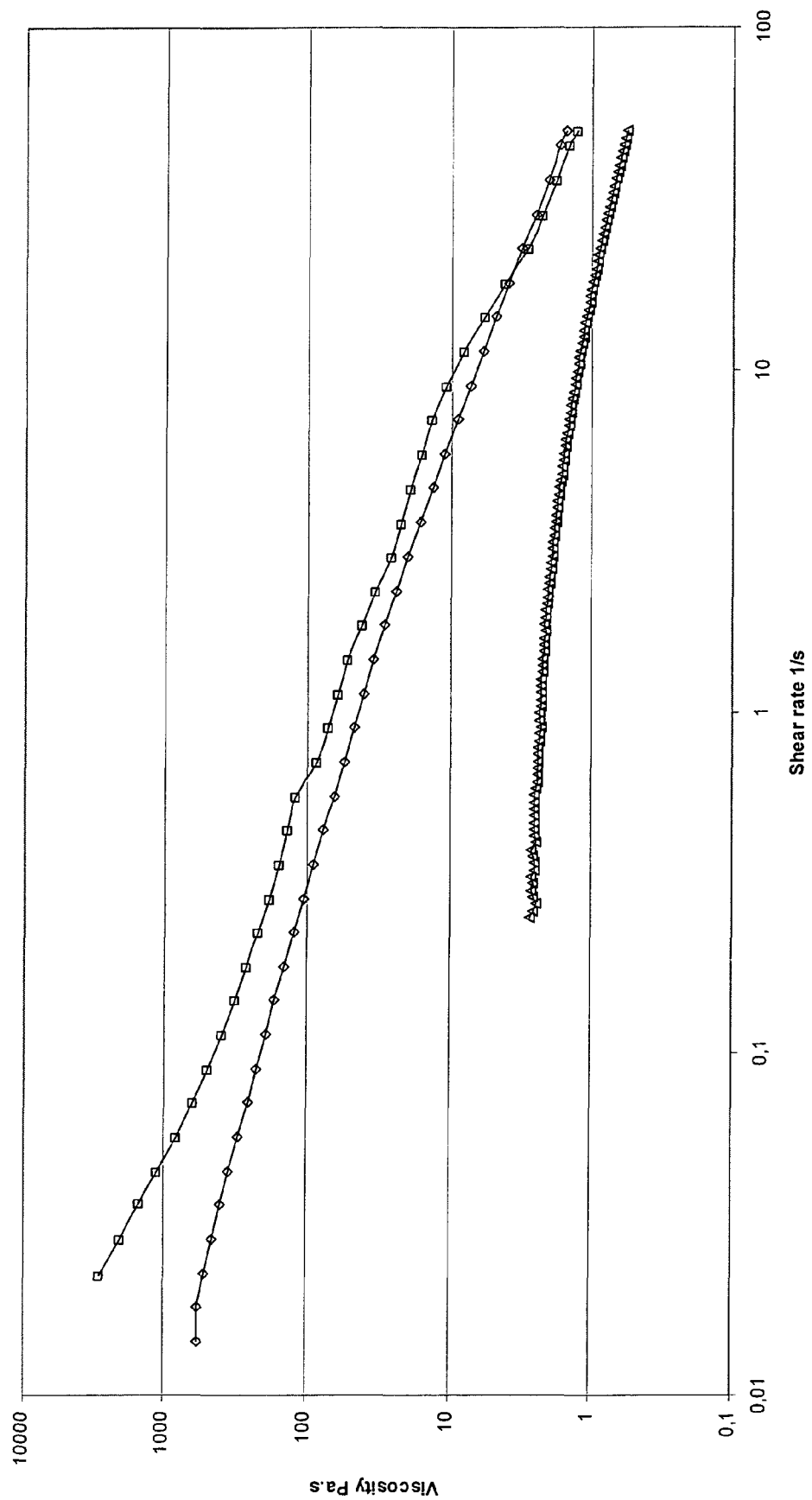
FIG. 3. Viscosity (Pa·s) as a function of the shear rate (s$^{-1}$); comparison of a commercial sample Synvisc® (curve with lozenges) with linear HA (natural HA) (curve with triangles) and HA derivatives of the invention (compounds of formula (I) according to the invention) (curve with squares) at 37° C. in the buffer.

The commercial sample (Synvisc®) taken as a reference is known to be solubilized in a buffer consisting of: 8.5 g/L NaCl, 0.05 g/L NaH$_2$PO$_4$, 0.6 g/L Na$_2$HPO$_4$; the samples of the compounds of the invention were prepared in the same solvent. The curves in FIG. 3 give the flow viscosity as a function of the shear rate for increasing shear rate.

From this figure it is demonstrated the role of the chemical modification on the viscosity of the linear HA; in addition, the viscosity obtained with the compounds of the invention is much greater than that of the reference product.

III—Dynamic Experiments

Figure 4:
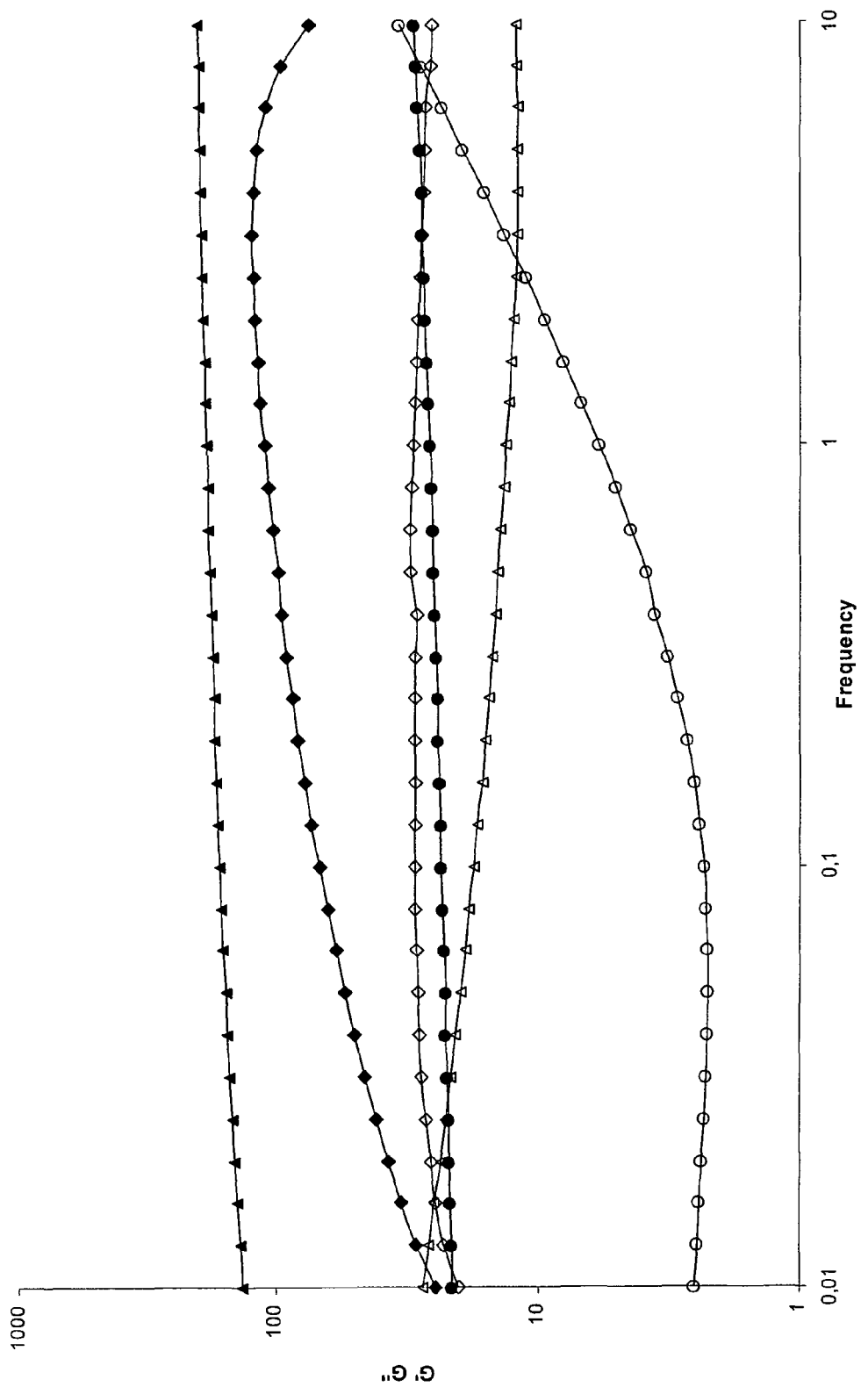
FIG. 4. Dynamic experiments G' (filled symbols) and G" (open symbols) as a function of the frequency at 37° C.: comparison of the results obtained from the reference HA (Synvisc® used as reference at 10 g/L) (lozenges) with those from HA derivatives of the invention of formula (I), i.e. 5C-10 at Mw=300,000 (circles), and 5-C10 at Mw=1.5×10$^6$ (triangles) at 10 g/L. HA of the invention are tested at 37° C. in buffer solution.

The results of these experiments are represented in FIG. 4.

Whatever the frequency used in the range 0.01 up to 30 Hz, there is no transition in G' and G" and G'>G". So whatever the frequency may be, all the derivatives prepared are mainly elastic, especially in comparison of the walking and running frequencies (0.5 and 2.5 Hz, respectively).

In the following table, few values of G' and G" are compared at 0.1 and 1 Hz from the previous figure data.

TABLE 1

Rheological characteristics at 37° C.

| | G' (0.1 Hz) | G" (0.1 Hz) | G' (1 Hz) | G" (1 Hz) |
|---|---|---|---|---|
| Reference c = 10 g/L | 69 | 30 | 112 | 30 |
| C = 10 g/L; HA Mw = 1.5 × 10$^6$ | 164 | 17 | 186 | 14 |
| C = 5 g/L; HA Mw = 1.5 × 10$^6$ | 22.50 | 1.92 | 24.65 | 1.36 |
| C = 10 g/L; HA Mw = 3 × 10$^5$ | 23 | 2 | 26 | 6 |

At 10 g/L, especially at low frequencies, modified HA has much higher G' values than that of the reference. This allows to assume that at a lower polymer concentration, also good performances (G',G" values) should be obtained (role of dilution is examined later).

IV—Influence of Polymer Concentration.

TABLE 2

Rheological characteristics of modified HA
M = 1.5 × 10$^6$ at 25° C.

| | G' (0.1 Hz) | G" (0.1 Hz) | G' (1 Hz) | G" (1 Hz) |
|---|---|---|---|---|
| C = 10 g/L; HA M = 1.5 × 10$^6$ | 200 | 116 | 226 | 13 |
| C = 8 g/L; HA M = 1.5 × 10$^6$ | 147 | 13 | 164 | 11 |
| C = 7 g/L; HA M = 1.5 × 10$^6$ | 93 | 9 | 103 | 6 |
| C = 6 g/L; HA M = 1.5 × 10$^6$ | 49 | 4 | 55 | 4 |
| C = 5 g/L; HA M = 1.5 × 10$^6$ | 34 | 3 | 37 | 2 |

At 25° C., especially at low frequencies, for concentrations ≧7 g/L, modified HA of formula (I) has much higher G' values than the reference Synvisc®. This confirms that at a lower polymer concentration, also good performances (G' and G" moduli) are obtained. It is proposed to use a polymer concentration lower than 10 g/L.

The present invention permits the use of less chemically modified HA injected to the patient for the same rheological effects compared to commercial products. That leads to reduce potential accumulation of non-biodegradable molecules in the knee articulation.

V—Enzymatic Degradation.

Enzymatic degradation was performed in the presence of 1 U/mg of compound of formula (I) in the buffer at 37° C. The hyaluronidase is provided by Sigma (H2251; lot: 70K0841 Type III from sheep testes EC No 253-464-3).

Figure 5:
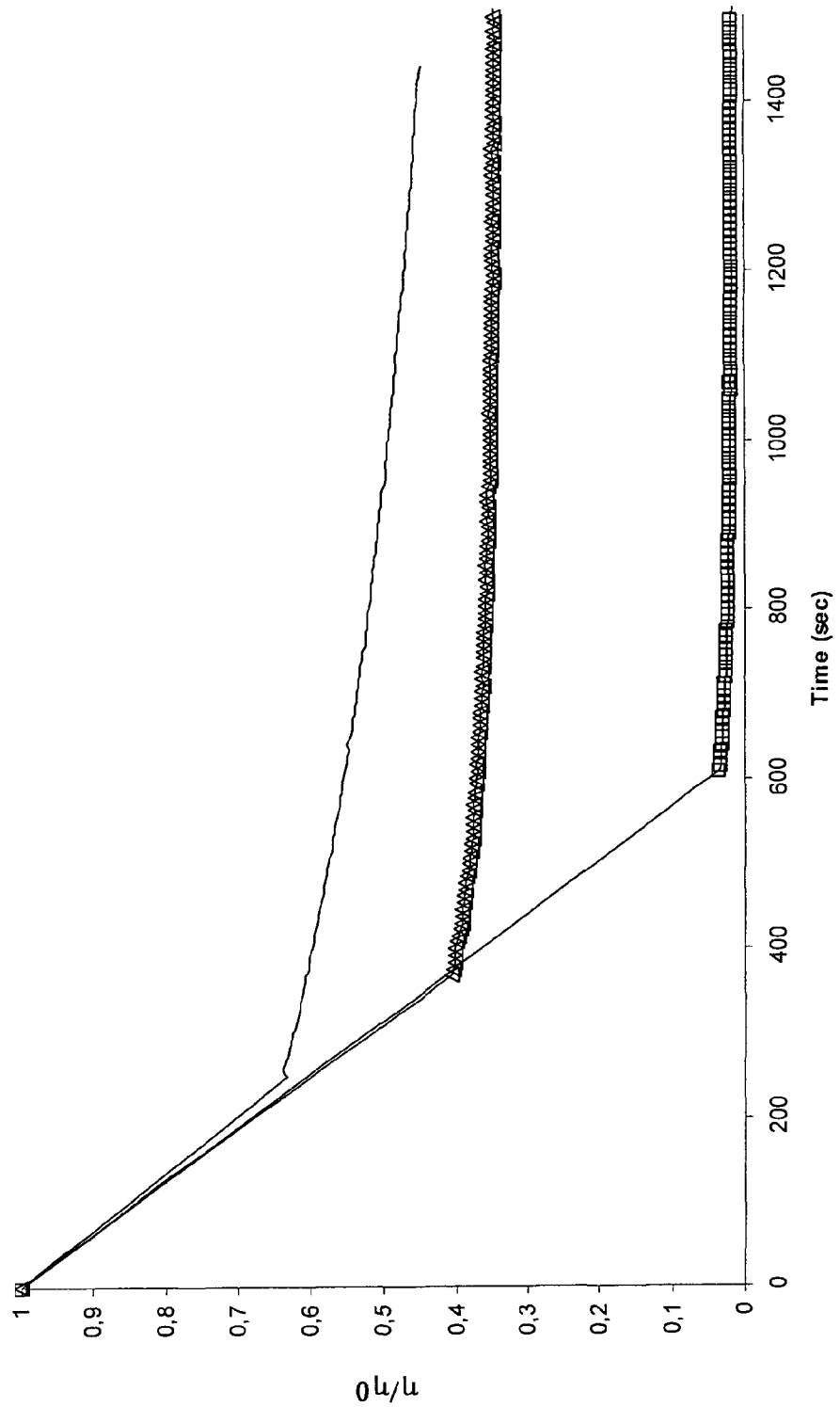
FIG. 5. Enzymatic degradation of the different samples at 37° C. in the buffer. The first rapid step occurs during the delay needed to start the rheology test. This Figure represents the reduced complex viscosity ratio ($\eta^*(t)/\eta^*_0$) with $\eta^*_0$ the initial value, as a function of time (in seconds) for linear HA (natural HA) (triangles), for HA-5C10 of the invention 1500 K (molecular weight of 1,500,000 g.mol$^{-1}$) (continuous line), and commercial reference (Synvisc®) (squares).

The dynamic rheological data are obtained at 1 Hz on the 10 g/L solutions and expressed as the modulus G'/initial value of G' (G'/G'$_0$) (data not shown) and as the ratio of the reduced complex viscosity ($\eta$*/initial value of $\eta$*($\eta$*$_0$)) as a function of time (FIG. 5).

From this drawing, it is clear that the compound of the invention has a better stability (its viscosity remains higher than the viscosity of the other samples) than the linear and the reference polymers. This effect is related to the mechanism of non covalent association involved in the amphiphilic polymers which behave as a self repairing polymer.

Compared to the reference (Synvisc®), the lower degradation of the molecules of the invention reinforces the fact that it is possible to maintain efficient rheological properties for the patient for a longer period. As a result, the time between two injections increases drastically and so there is an improvement of the patient's treatment comfort.

VI—Mixtures Comprising HA (Mw=1.5 10$^6$ g.mol$^{-1}$) and HA5-C10.

Rheology

A linear HA solution is mixed with a solution of derivative to get different proportion of each of the polymers in the mixture. The initial solutions are at 10 g/L in the buffer at 25° C.

Figure 6:
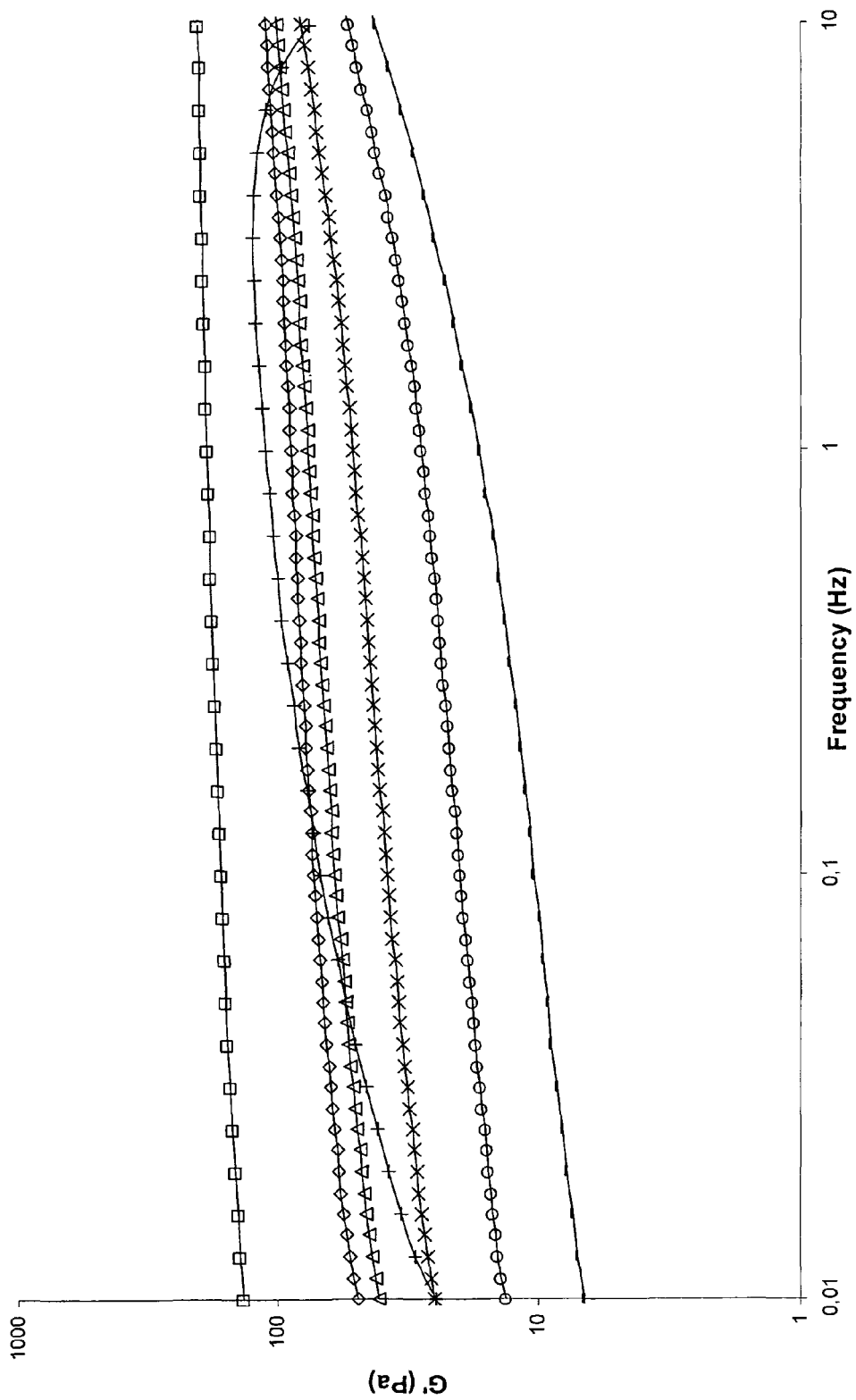
FIG. 6. Evolution of the elastic modulus G'(Pa) as a function of the frequency for mixtures HA/HA-5C10 of the invention (formula (I) with 5% of $R_i$ groups representing a group of formula (III) wherein p=10 and k=4). This Figure represents G' as a function of the frequency for the following products: Synvisc® (+), HA-5C10 of the invention (Mw=1.5×10$^6$ g/mol) alone (□), mixtures of HA-5C10 of the invention with HA (Mw=1.5×10$^6$ g/mol), comprising the following respective percentages of HA-5C10: 90% (◇), 80% (Δ), 70% (x), 60% (○), and 50% (−).

FIG. 6 shows the evolution of the elastic modulus G' as a function of the frequency for mixtures HA/HA-5C10. Said mixtures comprise from 0/100% to 50/50% in weight of HA and HA-5C10, and the total concentration in the mixed polymer solution is 10 g/L.

It can be noticed that the values of G' for mixtures 10/90 (90% of HA-5C10 and 10% of HA) and 20/80 (80% of HA-5C10 and 20% of HA) are close to the values of G' for the commercial reference (Synvisc®).

Figure 7:
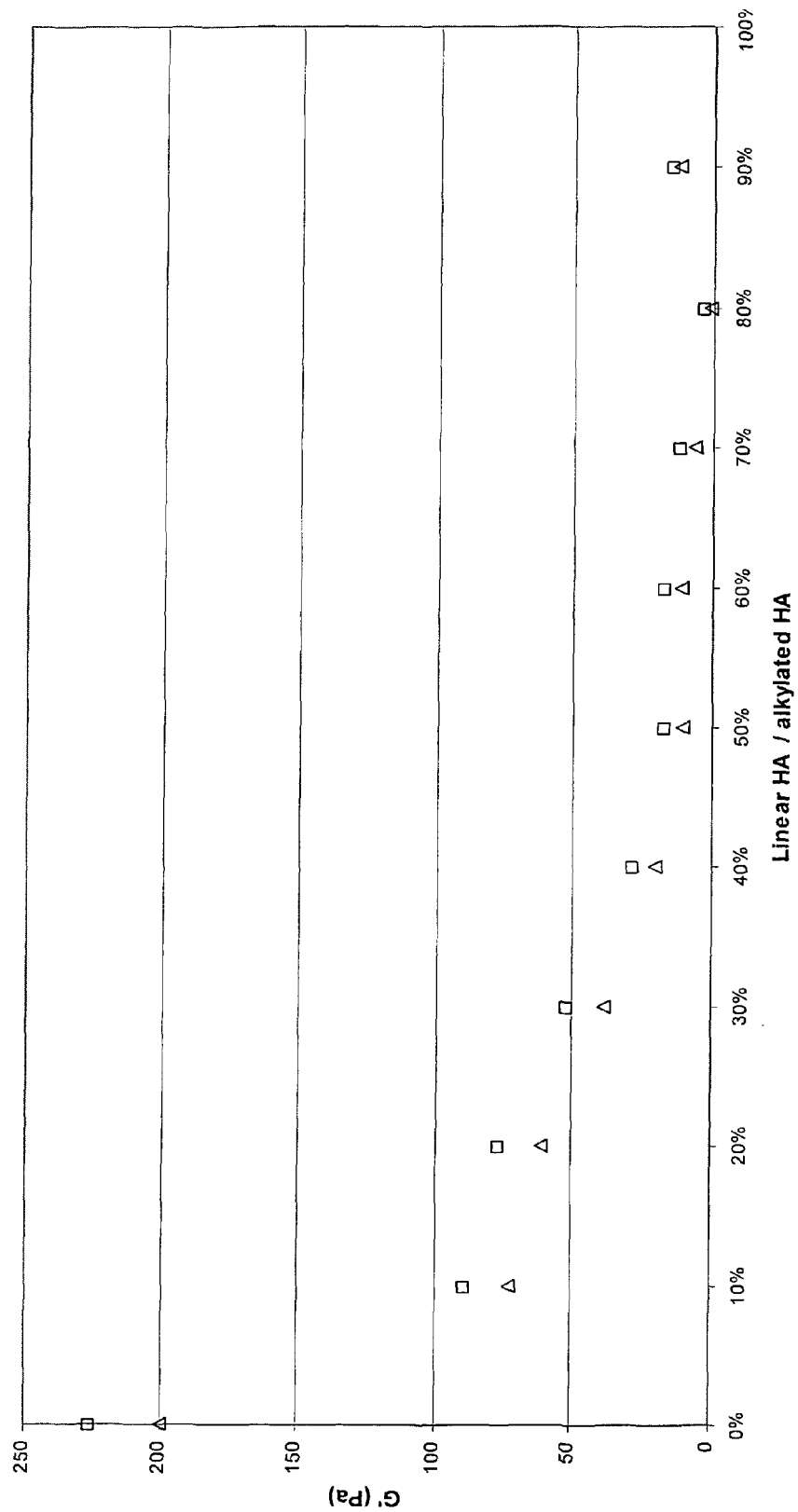
FIG. 7. Values of G' (Pa) at 1 (□) and 0.1 Hz (Δ) for mixtures of HA/HA-5C10 whose composition varies from 0/100% to 50/50% (weight percentages). The total concentration in polymer is 10 g/L in a buffer solution at 25° C.

From these data it is seen that a mixture including only 70% of the derivative has still good performances (high G' value compared to the reference). From these data, it is possible to determine G' values for two frequencies, namely 0.1 and 1 Hz. These data are represented on FIG. 7.

It can be noticed that up to 50/50%, since G" values are always lower than 15 Pa the elastic properties of the mixtures are maintained (G'>G").

VII—Use of α- and β-Cyclodextrins (α- and β-CD).

Figure 8:
FIG. 8. G' (Pa) (open symbols) and G" (Pa) (filled symbols) as a function of the frequency (Hz) for HA-5C10 of the invention at 10 g/L in NaCl 0.1 M at 25° C., alone (squares), or with 1 molar equivalent (triangles) or with 3 molar equivalents (circles) of natural α-CD (with regard to the alkyl chains in C10 with p=10).

The addition of one molar equivalent of α-cyclodextrin (α-CD) to the aqueous solution of HA-5C10 (Mw=1.5×10$^6$ g.mol$^{-1}$) induces an important reduction of G' and G" giving a better injectability. However, the resulting mixture (HA-5C10+α-CD) remains elastic (FIG. 8). After the in situ injection, the cyclodextrin is removed by diffusion and then recovering the formation of a gel.

Figure 9:
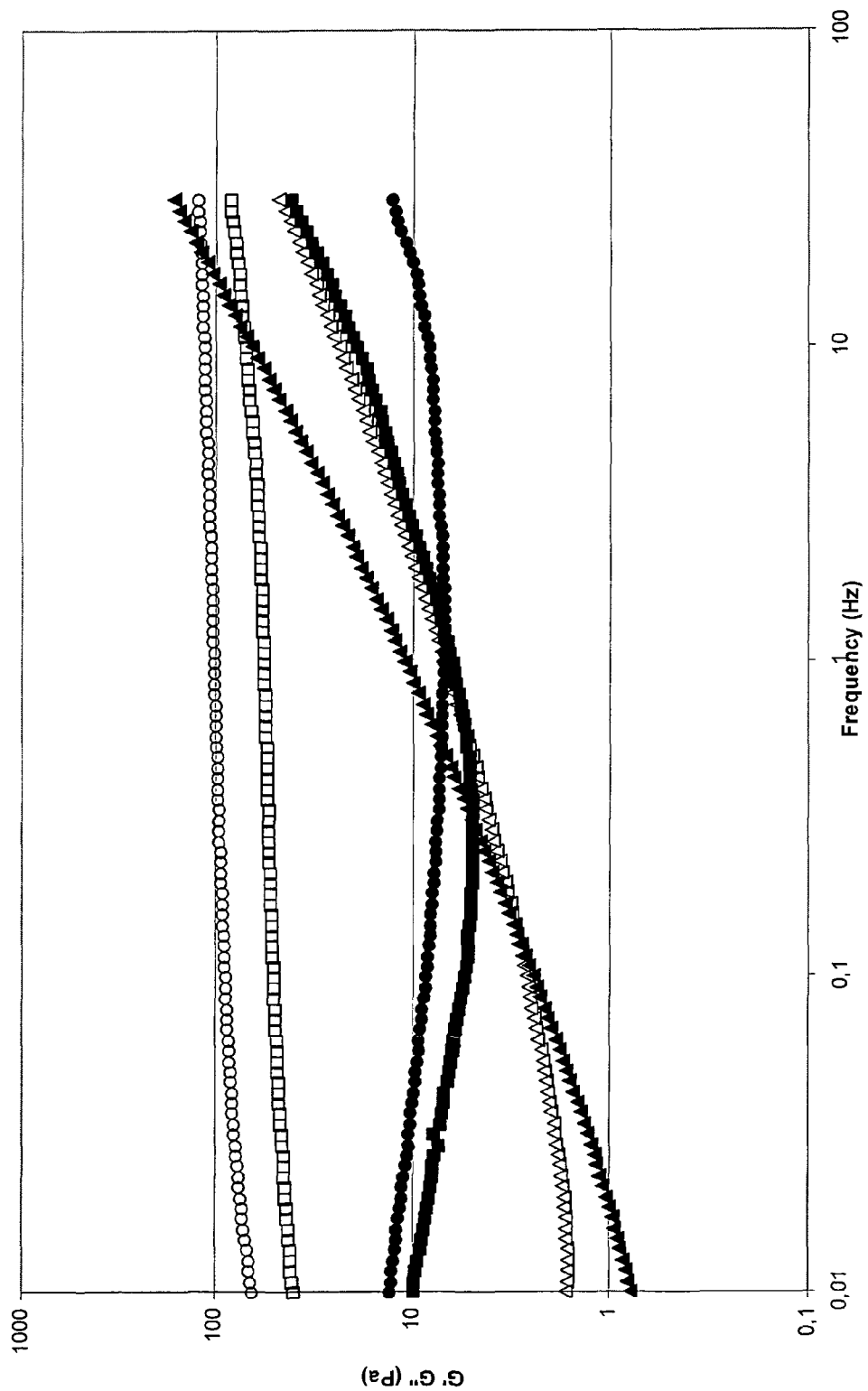
FIG. 9. G' (open symbols) and G" (filled symbols) as a function of the frequency (Hz) for HA-5C10 of the invention at 10 g/L in NaCl 0.1 M at 25° C., alone (circles), or with 1 molar equivalent (squares) and with 3 molar equivalents (triangles) of natural α-CD (with regard to the alkyl chains in C10 with p=10).

The value of G' is reduced of a factor of about 30. The β-cyclodextrin is less efficient (FIG. 9).

The reduction of the values of G' and G" by the addition of cyclodextrins facilitates the injection of HA-5C10.

The efficiency of CD is reflected by the modulus values given in Table 3. From these data, it is clear that cyclodextrins decrease the moduli of alkylated solution with a stronger effect of α-CD compared to β-CD. This will allow the filtration of the solution on small pores membranes (0.2 micrometer) while the reference (Synvisc®), being chemically crosslinked, could not be filtrated under the same conditions.

TABLE 3

Influence of CD on the rheology of alkylated HA ($Mw = 1.5 \times 10^6$ g·mol$^{-1}$).

|  | G' at 0.1 Hz (Pa) | G" at 0.1 Hz (Pa) |
| --- | --- | --- |
| Initial HA-C 10 | 87.8 | 8.49 |
| 1 equi α-CD | 3.46 | 1.32 |
| 1 equi β-CD | 49.59 | 5.45 |
| 3 equi α-CD | 2.75 | 0.71 |
| 3 equi β-CD | 2.68 | 2.46 |

Figure 10:
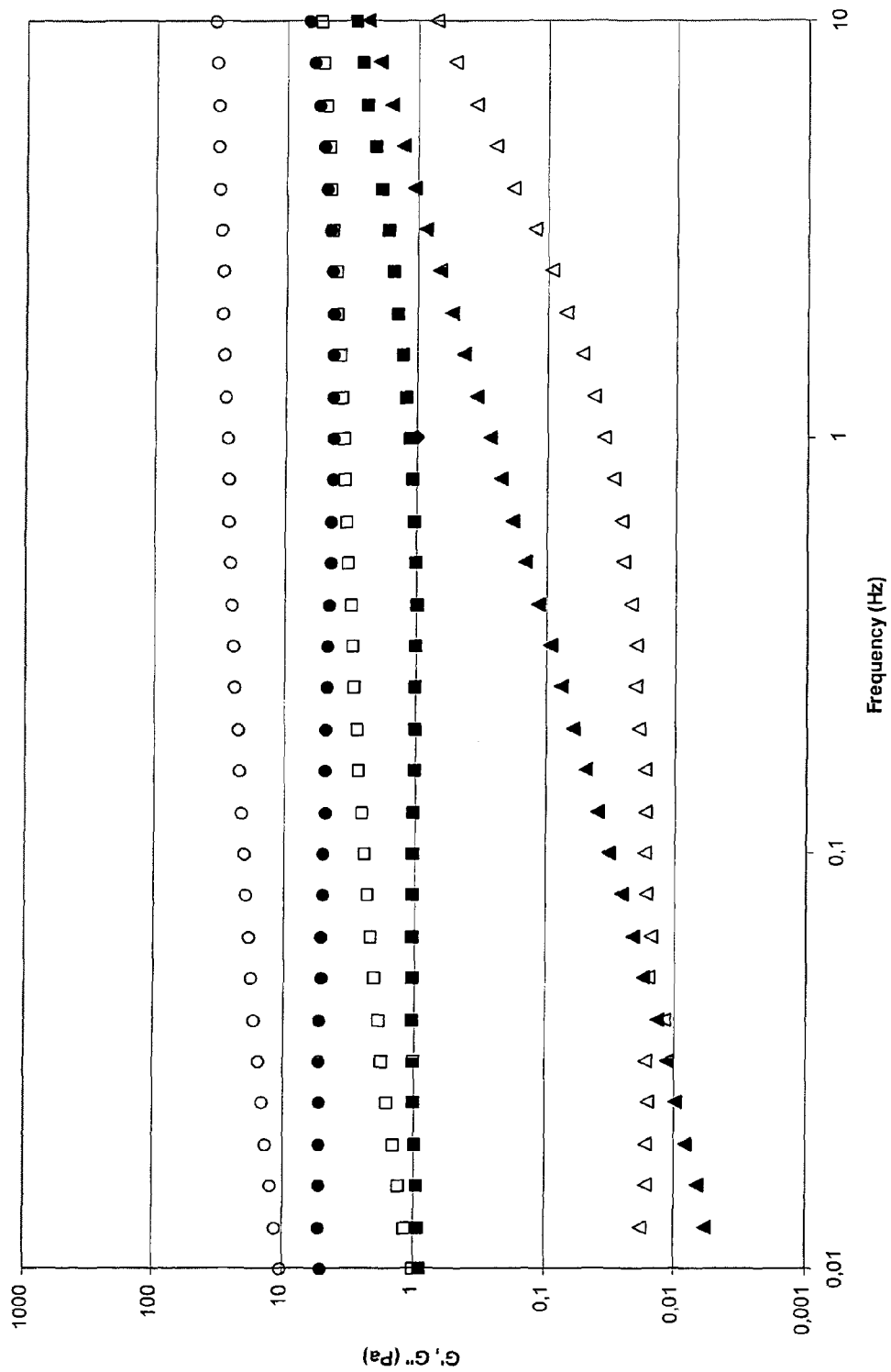
FIG. 10. G' (Pa) (open symbols) and G" (Pa) (filled symbols) as a function of the frequency (Hz) for HA-5C10 of the invention (Mw=300,000 g/mol) at 10 g/L in NaCl 0.1 M at 25° C., alone (circles), or with 1 molar equivalent (squares) or with 4 molar equivalents (triangles) of natural α-CD (with regard to the alkyl chains in C10 with p=10).

The same experiments were carried out with HA-5C10 with Mw=300,000 g.mol$^{-1}$. Similarly, the addition of one molar equivalent of α-cyclodextrin (α-CD) to the aqueous solution of HA-5C10 (Mw=300,000 g.mol$^{-1}$) induces an important reduction of G' and G" moduli (FIG. 10 and Table 4).

TABLE 4

Influence of CD concentration on the rheology of alkylated HA.

|  | G' at 0.1 Hz (Pa) | G" at 0.1 Hz (Pa) |
| --- | --- | --- |
| Initial HA-5C10 (M$_w$ 300,000 g/mol) | 20.03 | 5 |
| 1 equiv α-CD | 2.4 | 1.03 |
| 4 equiv α-CD | 0.01 | 0.03 |

VIII—Addition of Small Molecules to the Associative System.

Addition of Surfactants:

Addition of anionic surfactants to aqueous solutions of alkylated hyaluronic acid can result in pronounced effects on their rheological behaviour. Anionic surfactants in the presence of the alkylated hyaluronic acid lead to the formation of mixed micelles. Depending on the surfactant concentrations, the mixed micelles contain alkyl groups belonging to one or more polymer chains.

If the surfactant concentration is lower than the critical micellar concentration (CMC=concentration above which any added surfactant molecule appear as micellar aggregates) of said surfactant when it is alone in water, cross-linking between polymer chains occurs and is stronger compared to cross-linking between said polymer chains without surfactant, increasing the values of the rheological moduli. In this case, the micelles contain alkyl groups belonging to more than one polymer chain. Otherwise, if the concentration of the surfactant is higher than the CMC, the excess surfactant molecules interact separately with the grafted alkyl chains to form micelle-like aggregates; and the latter, by solubilising the alkyl chains, induce a decrease in the values of the moduli and a shift of the cross-over point of the G' and G" curves towards higher frequencies. In this case, the micelles contain alkyl groups belonging to one polymer chain.

Figure 11:
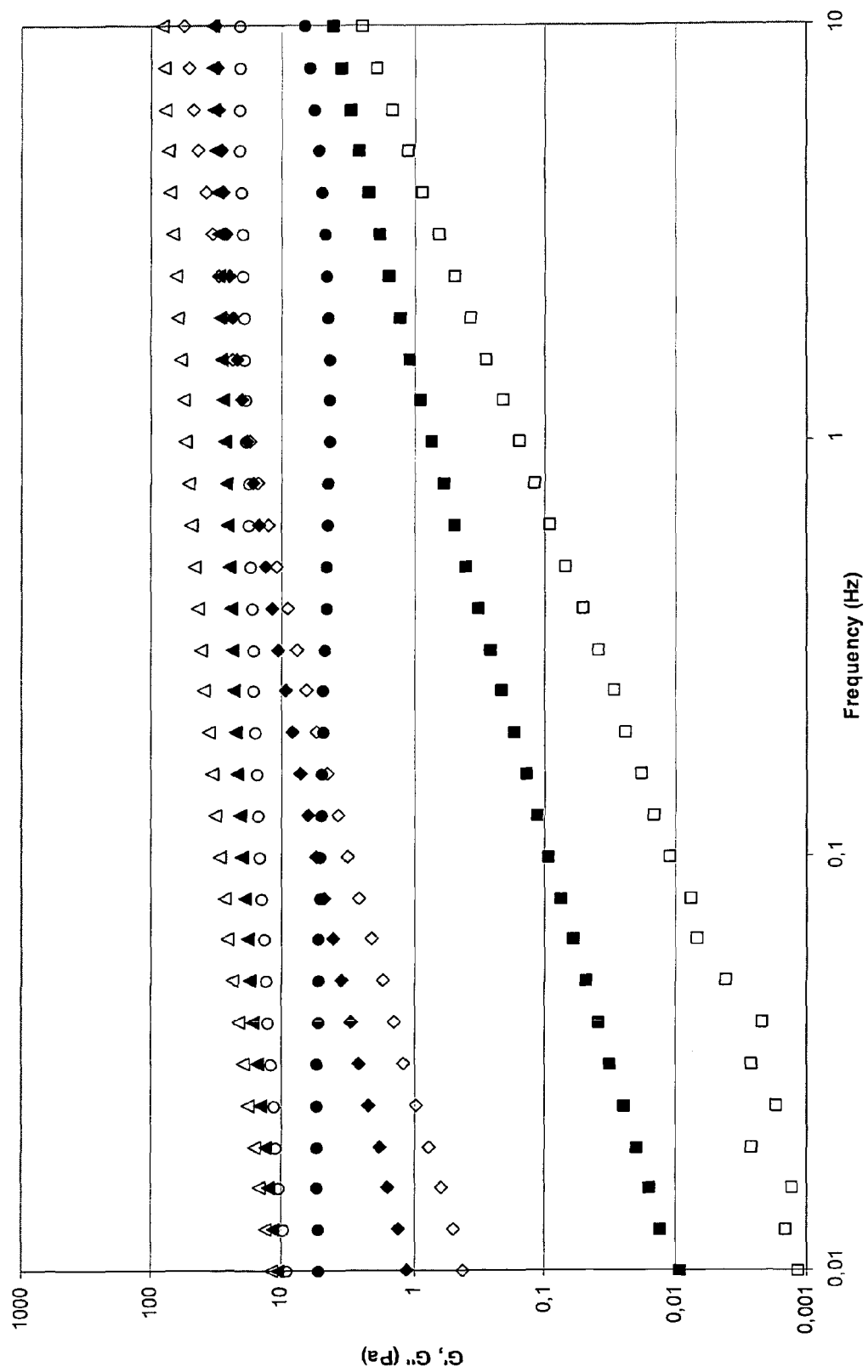
FIG. 11. G' (Pa) (open symbols) and G" (Pa) (filled symbols) as a function of the frequency (Hz) for HA-5C10 ($M_w$=300,000 g/mol) of the invention at 10 g/L in NaCl 0.1 M at 25° C., alone (circles), or with a concentration of sodium decyl sulphate (anionic surfactant) equal to CMC/4 (triangles), or with a concentration of sodium decyl sulphate equal to CMC (lozenges) or with a concentration of sodium decyl sulphate equal to 4CMC (squares) of sodium decyl sulphate, CMC corresponding to the critical micellar concentration of said anionic surfactant.

As can be seen from FIG. 11 and Table 5, addition of the anionic surfactant at a concentration of CMC/4 leads to an increase of the G' and G" moduli, although the G'/G" ratio is decreased. A viscoelastic solution behaviour is obtained at a surfactant concentration equal to the CMC. For surfactant concentrations higher than the CMC, a progressive dissolution of the physical network can be observed due to mixed micelle formation.

The reduction of the values of G' and G" by the addition of an excess amount of surfactant can facilitate the injection of HA-5C10.

TABLE 5

Influence of surfactant concentration on the rheology of alkylated HA.

|  | G' at 0.1 Hz (Pa) | G" at 0.1 Hz (Pa) |
| --- | --- | --- |
| Initial HA-5C10 (M$_w$ 300,000 g/mol) | 23.03 | 5 |
| Surfactant at CMC/4 | 20.60 | 14.47 |
| Surfactant at CMC | 3.11 | 5.46 |
| Surfactant at 4CMC | 0.01 | 0.09 |

The invention claimed is:
1. A method for preparing a viscoelastic composition, comprising:
adding to fluid a compound having the following formula (I):

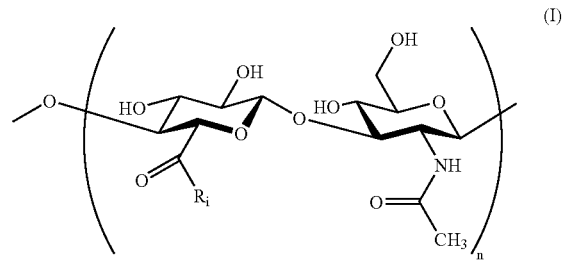

wherein:
n represents an integer varying from 720 to 6 200,
i varies from 1 to n,
R$_i$ represents:
OH,
OZ, wherein Z represents any monovalent counterion or any divalent counterion, or
a group of the following formula (II):

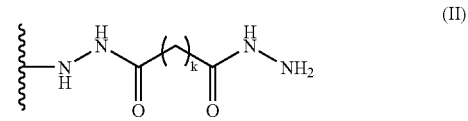

wherein:
k represents an integer varying from 1 to 17,
or a group of the following formula (III):

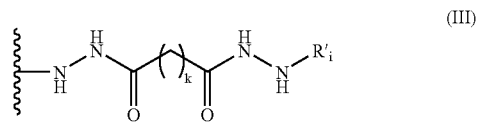

wherein:
k represents an integer varying from 1 to 17

R'$_i$ represents a linear or branched alkyl chain comprising p carbon atoms, wherein p is an integer varying from 1 to 17, with proviso that k+p is not greater than 28, and wherein at least one R$_i$ group represents a group of formula (III).

2. A method for cell culture, tissue engineering, soft tissue augmentation including the correction of facial wrinkles and scars, for viscosurgery, including eye surgery, for viscoprotection, for viscoseparation in post surgical applications, for passive drug delivery, and for viscosupplementation, comprising:

administering to a patient in need thereof of a compound having the following formula (I):

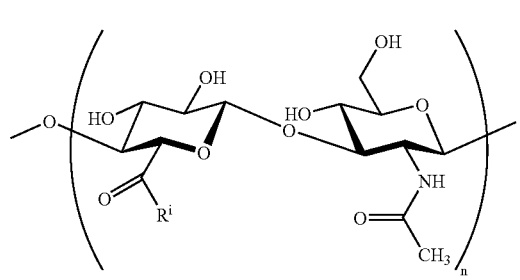

wherein:

n represents an integer varying from 720 to 6 200, i varies from 1 to n,

R$_i$ represents:

OH,

OZ, wherein Z represents any monovalent counterion or any divalent counterion, or a group of the following formula (II):

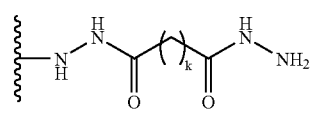

wherein:

k represents an integer varying from 1 to 17, or a group of the following formula (III):

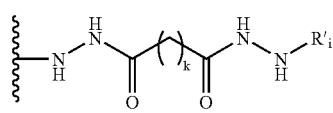

wherein:

k represents an integer varying from 1 to 17,

R'$_i$ represents a linear or branched alkyl chain comprising p carbon atoms, wherein p is an integer varying from 1 to 17, with the proviso that k+p is not greater than 28, and wherein at least one R$_i$ group represents a group of formula (III).

3. The method of claim 2, wherein the administered compound has the following formula (I):

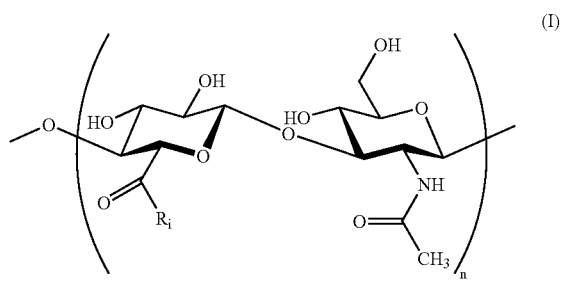

wherein:

n represents an integer varying from 720 to 6 200, i varies from 1 to n,

R$_i$ represents:

OH,

OZ, wherein Z represents any monovalent counterion or any divalent counterion, or a group of the following formula (II):

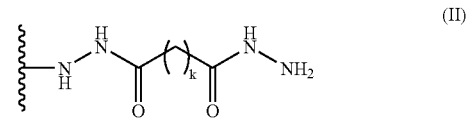

wherein:

k represents an integer varying from 1 to 17, or a group of the following formula (III):

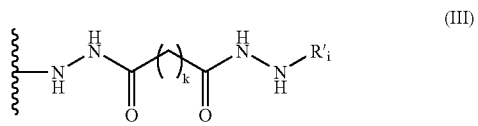

wherein:

k represents an integer varying from 1 to 17,

R'$_i$ represents a linear or branched alkyl chain comprising p carbon atoms, wherein p is an integer varying from 1 to 6, with the proviso that k+p is not greater than 20, and wherein at least one R$_i$ group represents a group of formula (III).

4. The method of claim 2, wherein the compound has the following formula (I):

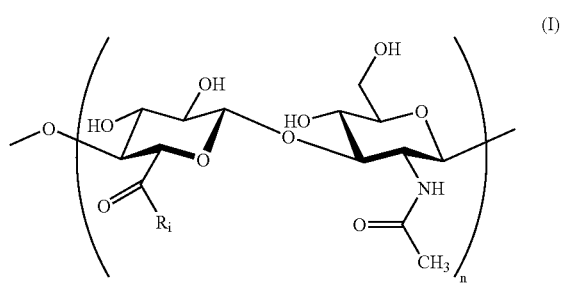

wherein:

n represents an integer varying from 720 to 6 200, i varies from 1 to n,

R$_i$ represents:

OH,
OZ, wherein Z represents any monovalent counterion or any divalent counterion, or
a group of the following formula (II):

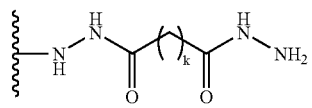
(II)

wherein:
k represents an integer varying from 1 to 17,
or a group of the following formula (III):

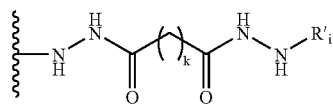
(III)

wherein:
k represents an integer varying from 1 to 17,
$R'_i$ represents a linear or branched alkyl chain comprising p carbon atoms, wherein p is an integer equal to or greater than 7,
with the proviso that k+p is not greater than 28,
and wherein at least one $R_i$ group represents a group of formula (III).

5. The method of claim 4, wherein from 2 to 30% of the total $R_i$ groups represent a group of formula (II) or (III).

6. The method of claim 4, wherein 8% of the total $R_i$ groups represent a group of formula (II) or (III).

7. A compound having the following formula (I):

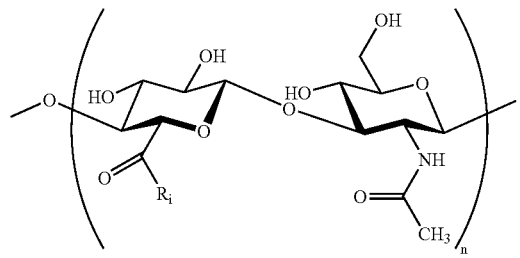
(I)

wherein:
n represents an integer varying from 720 to 6 200,
i varies from 1 to n,
$R_i$ represents:
OH,
OZ, wherein Z represents any monovalent counterion or any divalent counterion, or
a group of the following formula (II):

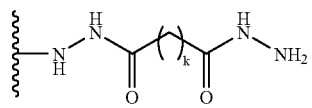
(II)

wherein k represents an integer varying from 1 to 17, or a group of the following formula (III):

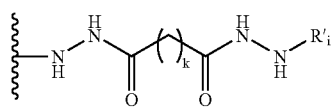
(III)

wherein:
k represents an integer varying from 1 to 17,
$R'_i$ represents a linear or branched alkyl chain comprising p carbon atoms, wherein p is an integer varying from 1 to 17,
with the proviso that k+p is not greater than 28,
and wherein at least one $R_i$ group represents a group of formula (III).

8. The compound of claim 7, wherein from 2 to 30% of the total $R_i$ groups represent a group of formula (II) or (III) as previously defined.

9. The compound of claim 7, wherein 8% of the total $R_i$ groups represent a group of formula (II) or (III) as previously defined.

10. The compound of claim 7, wherein k is equal to or greater than 4.

11. The compound of claim 7, having the following formula (I):

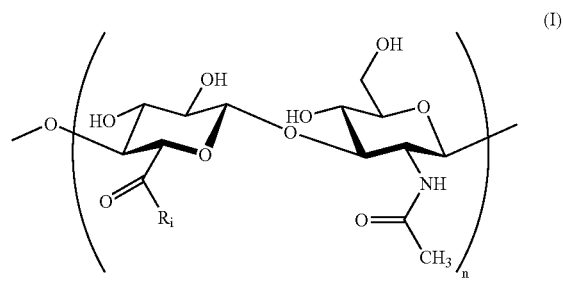
(I)

wherein:
n represents an integer varying from 720 to 6 200,
i varies from 1 to n,
$R_i$ represents:
OH,
OZ, wherein Z represents any monovalent counterion or any divalent counterion including, or
a group of the following formula (II-1):

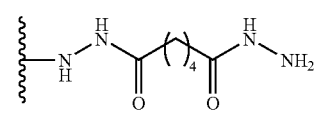
(II-1)

or a group of the following formula (III-1):

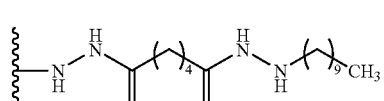
(III-1)

and wherein at least one $R_i$ group represents a group of formula (III-1).

12. A composition comprising a mixture of compounds of formula (I) as defined in claim 7.

13. A composition comprising a mixture of hyaluronic acid or its salts forms and of the compound as defined in claim 7.

14. A pharmaceutical composition, comprising a compound as defined in claim 7, in association with a pharmaceutically acceptable carrier.

15. A composition, in particular a pharmaceutical composition, comprising a compound as defined in claim 7, in association with an anionic surfactant.

16. A process for the preparation of compounds of formula (I):

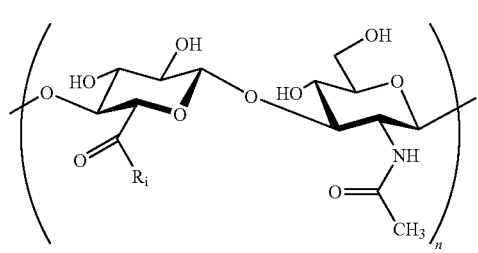
(I)

wherein:
n represents an integer varying from 720 to 6 200,
i varies from 1 to n,
$R_i$ represents:
OH,
OZ, wherein Z represents any monovalent counterion or any divalent counterion, or
a group of the following formula (II):

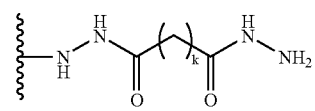
(II)

wherein:
k represents an integer varying from 1 to 17,
or a group of the following formula (III):

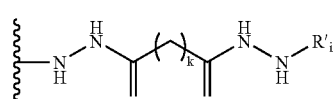
(III)

wherein:
k represents an integer varying from 1 to 17,
$R'_i$ represents a linear or branched alkyl chain comprising p carbon atoms, wherein p is an integer varying from 1 to 17,
with the proviso that k+p is not greater than 28,
and wherein at least one $R_i$ group represents a group of formula (III),
characterized in that it comprises the following steps:
reacting hyaluronic acid of formula (A):

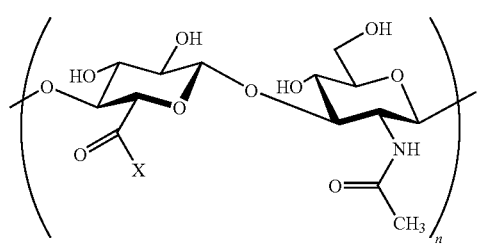
(A)

wherein:
X is OH or OZ, wherein Z represents any monovalent counterion or any divalent counterion,
n represents an integer varying from 720 to 6 200,
in the presence of a water-soluble coupling agent, including a water-soluble carbodiimide including EDC,
with a dihydrazide of formula (B):

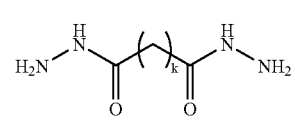
(B)

wherein k represents an integer varying from 1 to 17, to obtain a compound of formula (C):

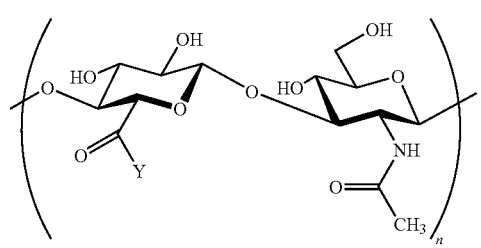
(C)

wherein Y is
OH or
OZ, Z being such as defined above, or
a group of formula (D):

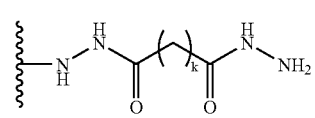
(D)

k being as defined above,
wherein at least one Y group represents a group of formula (D),
and reacting the compound of formula (C) in the presence of a reducing agent with an aldehyde comprising from 1 to 17 carbon atoms, to obtain a compound of formula (I) as defined above.

17. A process for the preparation of compounds of formula (I):

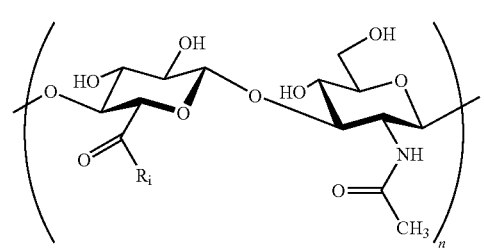
(I)

wherein:
n represents an integer varying from 720 to 6 200,
i varies from 1 to n,
$R_i$ represents:
OH,
OZ, wherein Z represents any monovalent counterion or any divalent counterion, or
a group of the following formula (II):

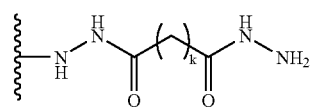
(II)

wherein k represents an integer varying from 1 to 17,
or a group of the following formula (III):

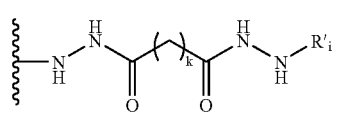
(III)

wherein:
k represents an integer varying from 1 to 17,
$R'_i$ represents a linear or branched alkyl chain comprising p carbon atoms, wherein p is an integer equal to or greater than 7,
with the proviso that k+p is not greater than 28,
and wherein at least one $R_i$ group represents a group of formula (III),
characterized in that it comprises the following steps:
reacting hyaluronic acid of formula (A):

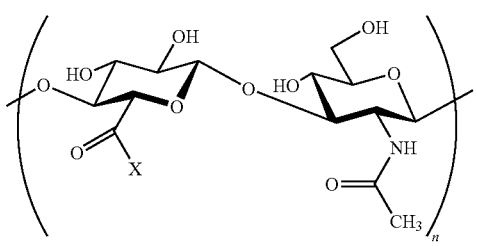
(A)

wherein:
X is OH or OZ, wherein Z represents any monovalent counterion including $Na^+$ or $K^+$ or any divalent counterion including $Ca^{2+}$ or $Mg^{2+}$,
n represents an integer varying from 720 to 6 200,
in the presence of a water-soluble coupling agent, including a water-soluble carbodiimide including EDC,
with a dihydrazide of formula (B):

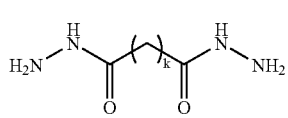
(B)

wherein k represents an integer varying from 1 to 17,
to obtain a compound of formula (C):

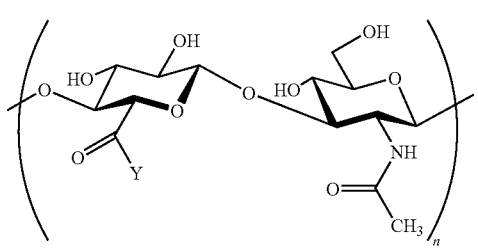
(C)

wherein Y is
OH or
OZ, Z being such as defined above, or
a group of formula (D):

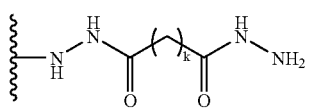
(D)

k being as defined above,
wherein at least one Y group represents a group of formula (D),
and reacting the compound of formula (C) in the presence of a reducing agent with an aldehyde comprising at least 7 carbon atoms, to obtain a compound of formula (I) as defined above.

18. A product such as obtained with the process of claim 17.

* * * * *